(12) United States Patent
Kelly

(10) Patent No.: US 7,378,397 B2
(45) Date of Patent: May 27, 2008

(54) TRH-DEGRADING ECTOENZYME INHIBITORS

(75) Inventor: Julie A. Kelly, Ballsbridge (IE)

(73) Assignee: The Provost, Fellows and Scholars of the College of the Holy and Undivided Trinity of Queen Elizabeth Near Dublin, Dublin (IE)

(*) Notice: Subject to any disclaimer, the term of this patent is extended or adjusted under 35 U.S.C. 154(b) by 13 days.

(21) Appl. No.: 11/345,649

(22) Filed: Feb. 1, 2006

(65) Prior Publication Data
US 2006/0293247 A1 Dec. 28, 2006

Related U.S. Application Data

(63) Continuation of application No. 10/223,590, filed on Aug. 19, 2002, now abandoned, which is a continuation-in-part of application No. PCT/IE01/00027, filed on Feb. 16, 2001.

(30) Foreign Application Priority Data
Feb. 17, 2000 (IE) ........................ 000135
Mar. 30, 2000 (IE) ........................ 000240

(51) Int. Cl.
A61K 38/06 (2006.01)
A61K 38/07 (2006.01)
A61K 38/08 (2006.01)
A61K 31/397 (2006.01)
A61K 31/40 (2006.01)
C07D 417/02 (2006.01)
C07D 413/02 (2006.01)

(52) U.S. Cl. .................... 514/22; 514/2; 514/18; 514/17; 514/210.02; 530/300; 530/329; 530/330; 530/331; 548/180; 548/200; 548/215

(58) Field of Classification Search ............... None
See application file for complete search history.

(56) References Cited

U.S. PATENT DOCUMENTS

| | | | | |
|---|---|---|---|---|
| 4,608,365 A | 8/1986 | Engel | ............... | 514/18 |
| 4,906,614 A | 3/1990 | Giertz et al. | ............... | 514/18 |
| 5,244,884 A | 9/1993 | Spatola et al. | ............... | 514/18 |
| 5,686,420 A | 11/1997 | Faden | ............... | 514/18 |

FOREIGN PATENT DOCUMENTS

WO    WO 88/09604    12/1988

OTHER PUBLICATIONS de Castiglione R and Angelucci F, Syntheses of Phyllomedusin and Uperolein, Peptide, Proceedings in European Peptide Symposium, 1976, 14: 529-533.*
Pages 132-135 from the search results including the structures associated with Reference U (de Castiglione) listed above.*

Bauer et al., "Inactivation of thyrotrophin-releasing hormone (TRH) by a TRH-specific ectoenzyme," *Cell-Surface Peptidases in Health and Disease* (Kenny, A. J., and Boustead, C.M., Eds.), Chapter 15: pp. 239-248, BIOS Scientific Publishers Limited, Oxford, UK, 1997.
Bauer et al., "Purification and characterization of the thyrotropin-releasing-hormone-degrading ectoenzyme," *Eur. J. Biochem.*, 224:387-396, 1994.

(Continued)

Primary Examiner—Anish Gupta
Assistant Examiner—Julie Ha
(74) Attorney, Agent, or Firm—Fulbright & Jaworski L.L.P.

(57) ABSTRACT

Peptide derivatives useful as inhibitors of activity of thyrotropin-releasing hormone-degrading ectoenzyme (TRH-DE) are of formula $I^a$:

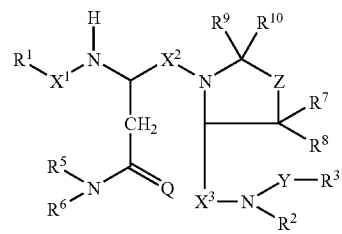

wherein:
$R^1$ is an optionally substituted 4-, 5- or 6-membered heterocyclic ring having one or more heteroatoms, in which at least one carbon atom of the ring is substituted with O or S;
$X^1$ is —CO— or —CS— or —CH$_2$CO— or CH($R^4$) wherein $R^4$ is H or optionally substituted alkyl or —COOH or —COOR$^{11}$ wherein $R^{11}$ is optionally substituted alkyl;
$X^2$ and $X^3$ (which may be the same or different) are —CO— or —CS—;
Z is —CH$_2$— or —S— or —O— or —NH—;
Q is O or S;
$R^2$ is H or optionally substituted alkyl or an optionally substituted carbocyclic ring;
$R^3$ is H or optionally substituted alkyl or an optionally substituted mono- or polycyclic ring, optionally having one or more heteroatoms in the ring(s) and optionally being a fused ring; or $R^2$ and $R^3$ together form an optionally substituted mono- or polycyclic ring optionally having one or more heteroatoms in the ring(s) and optionally being a fused ring;
$R^5$ and $R^6$ (which may be the same or different) are H, or lower alkyl;
$R^7$ and $R^8$ (which may be the same or different) are H, or optionally substituted lower alkyl;
$R^9$ and $R^{10}$ (which may be the same or different) are H, or optionally substituted alkyl, or an optionally substituted carbocyclic ring;
Y is —(CH$_2$)$_n$— where n is 0, 1, 2 or 3 provided that when $R^2$ and $R^3$ form part of the ring n is 0;
and pharmaceutically acceptable salts thereof.

18 Claims, 6 Drawing Sheets

OTHER PUBLICATIONS

Bauer et al., "Regulation and cellular localization of the membrane-bound thyrotropin-releasing hormone-degrading enzyme in primary cultures of neuronal, glial and adenohypophyseal cells," *Endocrinology*, 127:1224-1233, 1990.

Bauer, "Inactivation of thryotropin releasing hormone (TRH). The TRH-degrading enzyme as a regulator and/or terminator of TRH-signals?" *Metabolism of Brain Peptides* (O'Cuinn G., Ed.), Chapter 6: pp. 201-213, CRC Press, 1995.

Bennett et al., "TRH-catecholamine interactions in brain and spinal cord," *Ann. N. Y. Acad. Sci.*, 553:106-120, 1989.

Bissette et al., "Modification of pentobarbital-induced sedation by natural and synthetic peptides," *Neuropharmacology*, 17(45):229-237, 1978.

Burt and Snyder, "Thyrotropin releasing hormone (TRH): apparent receptor binding in rat brain membranes," *Brain Research*, 93:309-328, 1975.

Charli et al., Pyroglutamyl peptidase II inhibition specifically increases recovery of TRH released from rat brain slices, *Neuropeptides.*, 14:191-196, 1989.

Charli et al., "The narrow specificity pyroglutamate amino peptidase degrading TRH in rat brain is an ectoenzyme," *Neurochem. Int.*, 13:237-242, 1988.

Charli et al., "TRH inactivation in the extracellular compartment: role of pyroglutamyl peptidase II," *Neurobiology*, 6:45-57, 1998.

Cheng and Prusoff, "Relationship between the inhibition constant ($K_1$) and the concentration of inhibitor which causes 50 per cent inhibition ($I_{50}$) of an enzymatic reaction," *Biochem. Pharmacol.*, 22:3099-3108, 1973.

Cruz et al., "Neuronal localization of pyroglutamate aminopeptidase II in primary cultures of fetal mouse brain," *J. Neurochem.*, 56:1594-1601, 1991.

Dixon and Webb (eds.), *Enzymes*, 3rd Edition, pp. 72-75, Longman Group, London and Academic Press, New York, USA, 1979.

Drust and Connor, "Pharmacological analysis of shaking behavior induced by enkephalins, thyrotropin-releasing hormone or serotonin in rats: evidence for different mechanisms," *J. Pharmacol. Exp. Ther.*, 224:148-154, 1983.

Elmore et al., "Further characterization of the substrate specificity of a TRH hydrolysing pyroglutamate amniopeptidase from Guinea-pig brain," *Neuropeptides*, 15:31-36, 1990.

Ervin et al., "Thyrotropin-releasing hormone and amphetamine produce different patterns of behavioral excitation in rats," *Eur. J. Pharmacol.*, 72:35-43, 1981.

Fujiwara and Tsuru, "New chromogenic and fluorogenic substrates for pyrrolidonyl peptidase," *J. Biochem.*, 83:1145-1149, 1978.

Funk et al., "Role of central dopaminergic and 5-hydroxytryptaminergic projections in the behavioral responses elicited by thyrotropin-releasing hormone in rats," *Psychopharmacology*, 133:356-362, 1997.

Gallagher and O'Connor, "A study of a highly specific pyroglutamyl aminopeptidase type-II from the membrane fraction of bovine brain," *Int. J. Biochem. Cell Biol.*, 30:115-133, 1998.

Griffiths et al., "Comparative metabolism and conformation of TRH and its analogues," *Ann. N.Y. Acad. Sci.*, 553:217-231, 1989.

Griffiths, "Thyrotrophin releasing hormone: endocrine and central effects," *Psychoneuroendocrinol.*, 10:225-235, 1985.

Heuer et al., "The thyrotropin-releasing hormone-degrading ectoenzyme: the third element of the thyrotropin-releasing hormone-signaling system," *Thyroid*, 8:915-920, 1998.

Horita et al., "Pharmacology of thyrotropin-releasing hormone," *Rev. Pharmacol. Toxicol.*, 26:311-332, 1986.

Horita, "An update on the CNS actions of the TRH and its analogs," *Life Sci.*, 62:1443-1448, 1998.

Johnson et al., "A comparison of the motor behaviours produced by the intrathecal administration of thyrotrphin-releasing hormone and thyrotropin-releasing hormone analogues in the conscious rat," *Neuroscience*, 29:463-470, 1989.

Kelly et al., "Degradation of pyroglutamyl-phenylalanyl-proline amide by a pyroglutamyl aminopeptidase purified from membrane fractions of bovine brain," *Biochem. Soc. Trans.*, 25:114S, 1997.

Kelly et al., "Development of a continuous, fluorometric coupled enzyme assay for thyrotropin-releasing hormone-degrading ectoenzyme," *Analytical Biochem.*, 274:195-202, 1999.

Kelly et al., "Development of a discontinuous, quantitative HPLC assay for thyrotropin-releasing hormone-degrading ectoenzyme," *J. Neurochem.*, 73(Suppl.):S45, Abstract A, 1999.

Kelly et al., "Kinetic investigation of the specificity of porcine brain thyrotropin releasing hormone-degrading ectoenzyme for thyrotropin-releasing hormone-like peptides," *J. Biol. Chem.*, 275(22):16746-16751, 2000.

Kelly, "Thyrotropin-releasing hormone: basis and potential for its therapeutic use," *Essays in Biochem.*, 30:133-149, 1995.

Lanzara et al., "The use of analogues of TRH to probe the specificity of pyroglutamyl peptidase II[a]," *Ann. N.Y. Acad. Sci.*, 553:559-562, 1989.

Mazurov et al., "Effect of obligatory replacement and conformational restriction on psychotropic activity of thyroliberin analogs," *Russian Chemical Bulletin*, 47(10):1960-1964, 1998.

Mazurov et al., "Formation of pyroglutamylglutamine (or asparagine) diketopiperazine in 'non-classical' conditions: a side reaction in peptide synthesis," *Int. J. Peptide Proteins Res.*, 42:14-19, 1993.

Mitsuma and Nagimori, "Influence of the route of administration on thyrotropin-releasing hormone concentration in the mouse brain," *Experientia*, 39:620-622, 1983.

O'Cuinn et al., "Degradation of thyrotropin-releasing hormone and luteinising hormone-releasing hormone by enzymes of brain tissue," *J. Neurochem.*, 54:1-13, 1990.

O'Connor and O'Cuinn, "Purification of and kinetic studies on a narrow specificity synaptosomal membrane pyroglutamate aminopeptidase from guinea-pig brain," *Eur. J. Biochem.*, 150:47-52, 1985.

O'Connor and O'Cuinn, "Active site studies on a narrow-specificity thyroliberin-hydrolysing pyroglutamate aminopeptidase purified from synaptosomal membrane of guinea-pig brain," *J. Neurochem.*, 48:676-680, 1987.

O'Leary and O'Connor, "A study of a synaptosomal thyrotropin releasing hormone-inactivating pyroglutamate aminopeptidase from bovine brain," *Int. J. Biochem. Cell. Biol.*, 27:881-890, 1995.

Oliver et al., "Degradation of TRH and its analogues by rat serum and brain homogenate," *Biochem Biophys. Res. Commun.*, 84(4):1097-1102, 1978.

Schechter and Berger, "On the size of the active site in proteases. I. Papain," *Biochem. Biophys. Res. Comm.*, 27:157-162, 1967.

Turner, "Neuropeptide inactivation in the central nervous system," In: *Neuropeptide inactivation in the central nervous system*, (Kenny and Boustead, Eds.), Chapter 19: pp. 275-301, BIOS Scientific Publishers Limited, Oxford, UK, 1997.

Vonhof et al., "Norvaline[2]-TRH: binding to TRH receptors in rat brain homogenates," *Eur. J. Pharmacol.*, 180:1-12, 1990.

Walker, "Solid-phase peptide synthesis," In: *Peptide antigens—a practical approach*, Wisdom (ed.), Chapter 3: pp. 27-81, IRL Press, Oxford, UK, 1994.

Wilk and Wilk, "Rabbit brain pyroglutamyl peptidase II, a membrane-bound TRH degrading enzyme," *Neurochem. Int.*, 15:81-89 (556-558), 1989.

Wilk, "Inhibitors of TRH-degrading enzymes," *Ann. N.Y, Acad. Sci.*, 553:252-264, 1989.

Yamada et al., "Effects of behaviorally active doses of thyrotropin-releasing hormone and its analog MK-771 on dopaminergic neuronal systems in the brain of the rat," *Neuropharmacol.*, 23:735-739, 1984.

Zimmerman et al., "Sensitive assays for trypsin, elastase, and chymotrypsin using new fluorogenic substrates," *Anal. Biochem.*, 78:47-51, 1977.

* cited by examiner

TRH-DEGRADING ECTOENZYME INHIBITORS

This application is a continuation of co-pending application Ser. No. 10/223,590, filed Aug. 19, 2002, which claims priority to PCT Application Ser. No. PCT/IE01/00027, filed Feb. 16, 2001, and to Irish Applications IE 000135 and IE 000240, filed Feb. 17 and Mar. 30, 2000, respectively, the entire contents of these applications are incorporated by reference.

FIELD OF THE INVENTION

The present invention relates to certain peptide derivatives and uses thereof. In particular it relates to inhibitors of the enzyme Thyrotropin-releasing hormone-degrading ectoenzyme (TRH-DE), also known as pyroglutamyl aminopeptidase II (PAP-II) (EC 3.4.19.6). TRH-DE catalyses the removal of the N-terminal pyroglutamyl (Glp or pGlu) residue of the neuropeptide thyrotropin-releasing hormone (TRH) (1-4). TRH is a tripeptide with the primary structure L-pyroglutamyl-L-histidyl-L-prolineamide (Glp-His-ProNH$_2$). Compounds of the invention are useful as novel inhibitors of activity of the ectoenzyme TRH-DE and find application in investigating the role of the enzyme and the biological functions of its substrate, with potential therapeutic use as enzyme inhibitors in the field of medicine, particularly the treatment of brain and spinal injuries and central nervous system disorders.

BACKGROUND OF THE INVENTION

TRH has the structure:

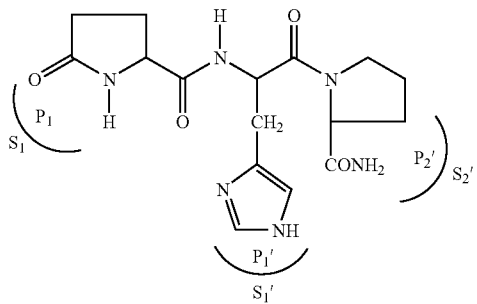

The nomenclature of Schechter and Berger (27) is used to describe the positions of the peptide substrate residues (P) relative to the scissile P$_1$—P$_1$' bond and the corresponding subsets (S) in the active site of the enzyme. In other literature, the right portion of the molecule is called the "prolineamide" or "C-terminal" portion; the centre portion of the molecule is called the "histidyl" portion; and the left portion of the molecule is called the "pyroglutamyl", "COOH-terminal" or "N-terminal" portion.

TRH was the first hypothalamic regulatory hormone to be characterised and as such plays a central role in regulating the pituitary-thyroid axis. In addition, TRH displays a broad spectrum of stimulatory CNS actions that are independent of the hypothalamic-pituitary-thyroid axis (5-7) and it is also now believed to function as a neurotransmitter and/or neuromodulator within the central nervous system (CNS) (5,6). Based on its CNS-mediated effects, TRH has been shown to have potential use in the treatment of brain and spinal injury and certain CNS disorders including cognitive deficits, epilepsy, and shock (7,8). The mechanisms by which TRH improves these clinical conditions are not yet clear but appear to be mediated, in part, by various other neurotransmitter systems (7,8). The full extent of the potential clinical usefulness of TRH cannot be realised until its functions in the CNS are entirely understood.

Unfortunately, the therapeutic efficacy of TRH is limited by its susceptibility to enzymatic degradation (8). Current evidence strongly indicates that TRH-DE is the principal enzyme responsible for the degradation of neuronally released TRH (9, 10-12). TRH-DE is located on synaptosomal membranes in the central nervous system (CNS) (13,14) and thus, it is strategically placed to play a significant role in controlling TRH signals within the CNS, much like that of acetylcholinesterase in regulating the neurotransmitter actions of acetylcholine. TRH-DE is the only ectoenzyme known to degrade TRH (15) and has been shown to exhibit a remarkably high specificity for TRH. Thus, TRH-DE appears to be an exceptional example of a neuropeptide-specific peptidase (16).

In general, potent and selective enzyme inhibitors are required for establishing the exact role of a particular enzyme and are also powerful tools for investigating the biological functions of the enzyme's substrate. In addition to providing valuable insights into the functional roles of enzymes and their substrates, enzyme inhibitors may be used therapeutically to enhance the clinical effects of an enzyme's substrate either by (a) potentiating the endogenous levels of the substrate and/or by (b) protecting endogenously administered substrate from degradation.

Thus, compounds that potently and selectively inhibit TRH-DE could be used to determine the role of TRH-DE in regulating TRH signals. Because TRH-DE displays a strict specificity for TRH, administration of TRH-DE inhibitors should only affect TRH'S neurotransmitter and/or neuromodulator actions. Therefore, TRH-DE inhibitors would also be particularly attractive for investigating the actions of TRH in the CNS. Furthermore, this exclusivity may offer a therapeutic advantage in cases where TRH-DE inhibitors are used to potentiate TRH's CNS actions. The design of TRH-DE inhibitors, however, is made difficult by TRH-DE's restricted specificity and by the lack of a 3D-structure for TRH-DE.

U.S. Pat. No. 4,608,365 Engel describes a treatment for the amelioration of symptoms of amyotrophic lateral sclerosis and other conditions which result from dysfunction of lower or upper motor neurons by the administration of doses of thyrotropin-releasing hormone by intravenous infusion or subcutaneous injection.

Specificity studies thus far indicate that TRH-DE substrates require a five-membered pyrrolidinone, thiazolidinone or butyrolactone ring in the P$_1$ position (4,17). In addition, several studies indicate that TRH-DE specificity is restricted to tri- or tetra-peptides containing the sequence Glp-His and that the presence of a histidine residue in the P$_1$' position is essential for TRH-DE activity (2,4,18-20). Recently, the inventor was the first to publish the observation that the naturally occurring TRH-like peptide Glp-Phe-ProNH$_2$ is also a substrate for TRH-DE whereas Glp-Glu-ProNH$_2$ is not (21). This finding has since been confirmed by Gallagher et al. (22). To date, no reports of other TRH-like peptides, with the general structure Glp-X-ProNH$_2$, acting as substrates or inhibitors of TRH-DE have been published.

Some tolerance in the P$_2$' position is suggested by the observations that both pyroglutamyl-histidyl-prolyl-β-naphthylamide (Glp-His-ProβNA) and pyroglutamyl-histidyl-prolylamido-4-methyl coumarin (Glp-His-ProAMC) are substrates for TRH-DE (4, 20, 22, 23). Glp-His-Trp is hydrolysed by TRH-DE (18) and substitution of the Pro residue in Glp-His-ProβNA by Ala or Trp does not appear to reduce turnover (4).

TRH and the C-terminally amidated peptides Glp-His-Pro-GlyNE$_2$ and Glp-His-GlyNH$_2$, have all been found to have lower K$_i$ values than their corresponding acids when examined as competitive substrates (24, 19, 22) leading to the suggestion that TRH-DE prefers an amide group at the carboxyl-terminus of peptide substrates (22). In addition, because the K$_m$ value observed for Glp-His-ProAMC was approximately ten times less than that for Glp-His-ProNH$_2$ Gallagher et al. (22) have proposed that TRH-DE has a preference for large hydrophobic groups at the carboxyl-terminus of substrates. On the contrary, using compounds present in this application, the inventor has now discovered that the addition of a large hydrophobic group to the C-terminus of TRH and TRH-like peptides causes a reduction in both the catalytic rate of hydrolysis and the specificity constant and that this is a useful feature to incorporate into an inhibitor not a substrate.

Only a few inhibitors have been synthesised that exhibit a significant effect on TRH-DE activity and none of these have been shown to be sufficiently effective for pharmacological studies in vivo (11,25). The most potent of these is N-[1(R,S)-carboxy-2-phenylethyl]-N-imidazole benzyl-histidyl β-naphthylamide (CPHNA) (26). Because CPHNA is not a TRH-DE substrate analogue, the specificity of the interactions of CPHNA with TRH-DE has been questioned (11). Nevertheless, CPHNA appears to reversibly inhibit TRH-DE with an inhibition constant (K$_i$) of 8 µM and to increase the recovery of TRH released from rat brain slices (26). These results indicate that TRH-DE inhibitors can be used to increase local TRH concentrations and that it may be possible to modulate TRH function in vivo via inhibition of TRH-DE activity.

U.S. Pat. No. 4,906,614 Giertz et al. describes a method of preventing or treating posttraumatic nervous injuries by administering a compound of the formula:

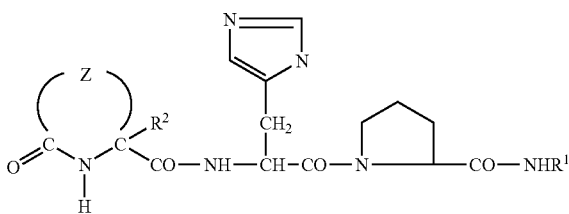

wherein R$^1$ is hydrogen, a lower alkyl group, cyclohexyl or benzyl; Z is one of the groups

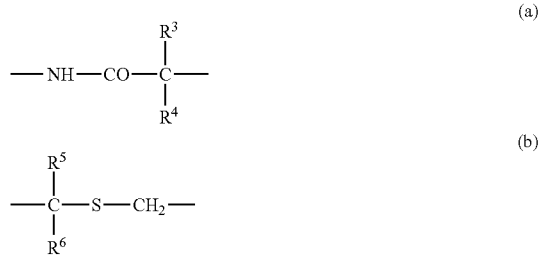

if Z is a group (a), R$^2$ and R$^3$ together represent an additional bond between the carbon atoms bearing them, or if Z represents a group (b), R$^3$ is hydrogen; R$^4$ is hydrogen or lower alkyl; R$^5$ is hydrogen, lower alkyl or phenyl, R$^6$ is hydrogen or methyl.

U.S. Pat. No. 5,244,884 Spatola et al. describes thionated analogues of thyrotropin releasing hormone, having the formula:

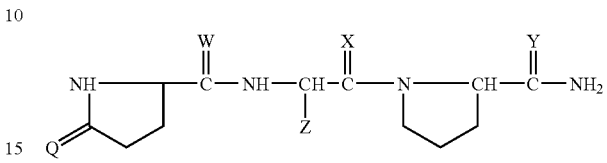

wherein,

Q, W, X and Y, same or different, are oxygen or sulphur, with the proviso that at least one of Q, W, X and Y is always sulphur;

Z is lower alkyl or (4-imidazolyl)methyl; and the pharmaceutically acceptable salts thereof. The disclosed compounds are stated to highly and selectively bind to TRH binding sites in animal tissues, and their utility in treating a variety of diverse physical conditions is disclosed.

U.S. Pat. No. 5,686,420 Faden describes a series of novel thyrotropin-releasing hormone analogs wherein the C-terminal prolineamide moiety has been preserved, the N-terminal moiety comprises one of five different ring structures and the histidyl moiety is substituted with CF$_3$, NO$_2$ or a halogen. A method of use of the analog for the treatment of neurologic disorders in also provided.

The contents of each of the above-mentioned U.S. Patents is incorporated herein by reference.

The present invention relates to compounds that competitively inhibit TRH-DE and display greater apparent binding affinities (i.e. lower K$_i$ values) for TRH-DE than the endogenous substrate, TRH. These compounds have not been reported to occur naturally. Searches carried out after the priority date of this application have revealed that one of the compounds has been named in published papers.

Burt D. R et al., *Brain Research*, 93 (1975) 309-328 mention pGlu-Asn-ProNH$_2$ as one of 25 analogues of TRH used in tests of inhibition of TRH binding in the cerebral cortex and pituitary.

Bissette G. et al., *Neuropharmacology* (1978) 17 (45), 229-37 list pGlu-Asn-Pro-NH$_2$ (Abbott 43689) as a TRH analogue used in tests of analeptic effect in mice.

Mazurov A. A. et al., *Russian Chemical Bulletin* (1998) 47 (10) 19601964 describe the preparation of (inter alia) Glp-Asn-ProNH$_2$ and the measurement of the antidepressant activity of the compound in rats.

Mazurov A. A. et al., *Int. J. Peptide Proteins Res*. (1993) 42, 14-19 describe the synthesis of Glp-Asn-ProNH$_2$.

Oliver C. et al., *Biochem Biophys. Res. Commun*. (1978) 84 (4) 1097-1102 refer to pGlu-Asn-Pro-NH$_2$ as one of 30 TRH analogues subjected to enzymic degradation by rat serum or brain homogenate.

None of these papers discloses or suggests the use of Glp-Asn-ProNH$_2$ as an inhibitor of activity of TRH-DE and there is nothing in their teaching to indicate the line of research leading to the present invention.

All of the other compounds of the invention are believed to be novel.

SUMMARY OF THE INVENTION

In one aspect the present invention provides novel compounds of the formula I:

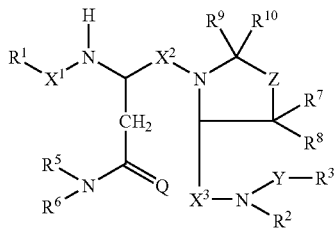

wherein:

$R^1$ is an optionally substituted 4-, 5- or 6-membered heterocyclic ring having one or more heteroatoms, in which at least one carbon atom of the ring is substituted with O or S;

$X^1$ is —CO— or —CS— or —CH$_2$CO— or CH($R^4$) wherein $R^4$ is H or optionally substituted alkyl or —COOH or —COOR$^{11}$ wherein $R^{11}$ is optionally substituted alkyl;

$X^2$ and $X^3$ (which may be the same or different) are —CO— or —CS—;

Z is —CH$_2$— or —S— or —O— or —NH—;

Q is O or S;

$R^2$ is H or optionally substituted alkyl or an optionally substituted carbocyclic ring;

$R^3$ is H or optionally substituted alkyl or an optionally substituted mono- or polycyclic ring, optionally having one or more heteroatoms in the ring(s) and optionally being a fused ring; or $R^2$ and $R^3$ together form an optionally substituted mono- or polycyclic ring optionally having one or more heteroatoms in the ring(s) and optionally being a fused ring;

$R^5$ and $R^6$ (which may be the same or different) are H, or lower alkyl;

$R^7$ and $R^8$ (which may be the same or different) are H, or optionally substituted lower alkyl;

$R^9$ and $R^{10}$ (which may be the same or different) are H, or optionally substituted alkyl, or an optionally substituted carbocyclic ring;

Y is —(CH$_2$)$_n$— where n is 0, 1, 2 or 3 provided that when $R^2$ and $R^3$ form part of the ring n is 0;

provided that when $R^1$ is:

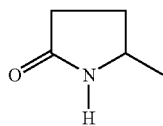

and $X^1$, $X^2$ and $X^3$ are —CO—
and $R^5$, $R^6$, $R^7$, $R^8$, $R^9$, $R^{10}$ are H
and Z is CH$_2$
and Q is O
and Y is —(CH$_2$)$_n$— where n is 0,
then $R^2$ and $R^3$ are not both H;
and pharmaceutically acceptable salts thereof.

In another aspect the present invention provides compounds of the formula I as defined above and pharmaceutically acceptable salts thereof for use in a method for treatment of the human or animal body by therapy or a diagnostic method practised on the human or animal body. Glp-Asn-ProNH$_2$ is disclaimed in formula I.

In a further aspect the present invention provides compounds of formula I$^a$:

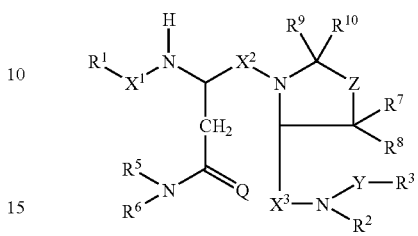

wherein:

$R^1$ is an optionally substituted 4-, 5- or 6-membered heterocyclic ring having one or more heteroatoms, in which at least one carbon atom of the ring is substituted with O or S;

$X^1$ is —CO— or —CS— or —CH$_2$CO— or CH($R^4$) wherein $R^4$ is H or optionally substituted alkyl or —COOH or —COOR$^{11}$ wherein $R^{11}$ is optionally substituted alkyl;

$X^2$ and $X^3$ (which may be the same or different) are —CO— or —CS—;

Z is —CH$_2$— or —S— or —O— or —NH—;

Q is O or S;

$R^2$ is H or optionally substituted alkyl or an optionally substituted carbocyclic ring;

$R^3$ is H or optionally substituted alkyl or an optionally substituted mono- or polycyclic ring, optionally having one or more heteroatoms in the ring(s) and optionally being a fused ring; or $R^2$ and $R^3$ together form an optionally substituted mono- or polycyclic ring optionally having one or more heteroatoms in the ring(s) and optionally being a fused ring;

$R^5$ and $R^6$ (which may be the same or different) are H, or lower alkyl;

$R^7$ and $R^8$ (which may be the same or different) are H, or optionally substituted lower alkyl;

$R^9$ and $R^{10}$ (which may be the same or different) are H or optionally substituted alkyl or an optionally substituted carbocyclic ring;

Y is —(CH$_2$)$_n$— where n is 0, 1, 2 or 3 provided that when $R^2$ and $R^3$ form part of the ring n is 0;

and pharmaceutically acceptable salts thereof, for use as an inhibitor of activity of TRH-DE.

The invention also provides compounds of formula I$^a$ as defined above and pharmaceutically acceptable salts thereof for use in potentiating endogenous TRH and/or in protecting exogenously administered TRH or TRH analogues from degradation by TRH-DE.

In particular embodiments, $R^5$ and $R^6$ are H and Q is O, so that the TRH derivatives have L-asparagine residue (Asn) in the P$_1$' position.

According to one aspect, the invention relates to a series of novel TRH derivatives having L-asparagine (Asn) in the P$_1$' position of the peptide with the general formula:

$R^1$-X$^1$-L-Asn-L-Pro-NR$^2$Y R$^3$, 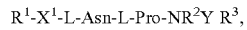

where $R^1$, $X^1$, $R^2$, Y and $R^3$ are as defined above.

Suitably, Z is —CH$_2$ and $R^7$ and $R^8$ are H.

In preferred embodiments $X^1$, $X^2$ and $X^3$ are —CO—

In any of the optionally substituted derivatives defined above, suitable substituents may be present which do not interfere substantially with the function of the compounds as inhibitors of TRH-DE activity. Examples of ring substituents include oxo, thioxo, alkyl, alkenyl, alkynyl, aryl, alkoxy, halo, haloalkyl, nitro, azido, cyano, hydroxyl, hydroxyalkyl, $SO_nR^{14}$ where $R^{14}$ is alkyl and n=0, 1 or 2, or a carboxyl or ester group of the formula —$COOR^{15}$ where $R^{15}$ is H or alkyl and which may be in ionic form —$COO^-$. Examples of substituents on alkyl groups (including alkyl groups in ring substituents mentioned in the preceding sentence) include halo, nitro or cyano. Optional hetero atoms in the ring(s) of $R^3$, or $R^2$ and $R^3$ together, include N, O or S. Suitably there may be from 1-3 hetero atoms per ring, and the hetero atoms in any ring may be the same or different.

An alkyl, alkenyl, alkynyl, or alkoxy group may be straight chain or branched and suitably contains from 1 to 20, more suitably from 1 to 10, most suitably from 1 to 5 carbon atoms. A lower alkyl group suitably contains 1 to 5 carbon atoms. Halo includes iodo, bromo, chloro or fluoro. A carbocyclic ring or a mono- or polycyclic ring suitably contains from 4 to 20 ring atoms, more suitably 4 to 8 ring atoms per ring, most suitably in the case of a polycyclic ring a total of 8 to 16 ring atoms, any ring atoms which are not hetero atoms being carbon atoms.

Suitably $R^2$ is H or $C_1$-$C_5$ alkyl. Suitably Y is —$(CH_2)_n$— where n is 0 or 1. Desirably $R^3$ is: optionally substituted alkyl, more particularly $C_1$-$C_5$ alkyl, such as propyl or isopropyl; an optionally substituted monocyclic ring, such as optionally substituted phenyl or cyclohexyl; an optionally substituted monocyclic ring having one or two heteroatoms in the ring, such as optionally substituted thiazolyl; an optionally substituted polycyclic ring, such as optionally substituted naphthyl or tetrahydronaphthyl; an optionally substituted polycyclic ring having one or two heteroatoms in the ring, such as optionally substituted chromene (particularly optionally substituted coumarin), quinoline or isoquinoline; any of the foregoing rings optionally having a benzo ring fused thereto (particularly benzocoumarin). In a particular embodiment, $R_3$ may be doubly substituted alkyl. The alkyl group may be substituted with the side chain of an amino acid or with an amidated carboxyl group. $R_3$ may be an amino acid residue which is optionally substituted. Among optional substituents, particular substituents include $C_1$-$C_5$ alkyl or trihaloalkyl, $C_1$-$C_5$ alkoxy (particularly methoxy), hydroxyl, oxo or halo.

Alternatively $R^2$ and $R^3$ together may form an optionally substituted monocyclic or polycyclic ring such as piperazinyl. Suitably $R^2$ or $R^3$, or $R^2$ and $R^3$ together, represent a hydrophobic group, particularly a large hydrophobic group such as methyl coumarin.

In particular preferred embodiments $R^3$ is phenyl, optionally having 1 or 2 substituents selected from $C_1$-$C_5$ alkyl or trihaloalkyl, $C_1$-$C_5$ alkoxy, hydroxyl, and/or halo; or coumarin optionally substituted with $C_1$-$C_5$ alkyl or trihaloalkyl; or naphthyl; or tetrahydronaphthyl.

Suitably $R^3$ is an optionally substituted mono- or polycyclic ring having up to 10 ring atoms.

Most suitably $R^3$ includes an optionally substituted phenyl ring. In preferred embodiments, —$N(R^2)$ Y $R^3$ has a group $R^3$ which includes O spaced from the N by 1, 2 or 3 C atoms, particularly 3 atoms as in 7-amido coumarin.

Certain preferred compounds of the invention include the secondary amine structure

where Y and $R^3$ are as defined above.

The group —$N(R_2)YR_3$ or the group $R_3$ may be at least one amino acid residue. The amino acid may be substituted. The substitution may be by one or more amino acids themselves optionally substituted. The substitution may be by a hydrophobic group. The amino acid may be amidated. Suitable hydrophobic groups include optionally substituted coumarin such as methyl coumarin or 7-amino 4-methyl coumarin. The amino acids may suitably be neutral amino acids.

One group of preferred compounds has an N-substituted amide group at the C-terminus of Glp-Asn-Pro.

Another group of preferred compounds are those in which the group —$N(R_2)YR_3$— is at least one amino acid residue. Particularly preferred are compounds in which —$N(R_2)Y R_3$— is Tyr-TrpAMC or TrpAMC.

$R^1$ may suitably be:

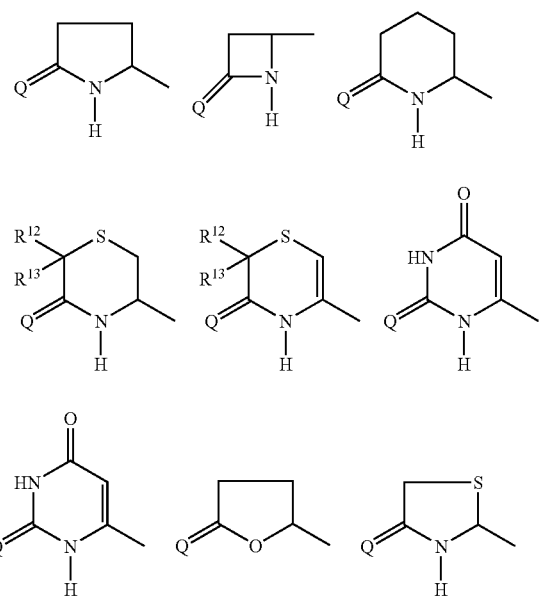

wherein $R^{12}$ is hydrogen, lower alkyl or phenyl,
$R^{13}$ is hydrogen or lower alkyl,
Q is O or S.

In preferred embodiments, Q is O. Most suitably $R^1$ is a five-membered heterocyclic ring, particularly a pyrrolidinone, thiazolidinone or butyrolactone ring.

In particular preferred embodiments, $R^1$ is

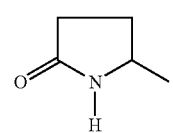

The Following are Examples of Compounds of Formula I[a]:
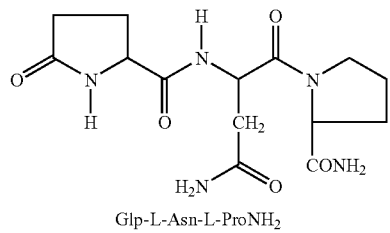
Glp-L-Asn-L-ProNH$_2$
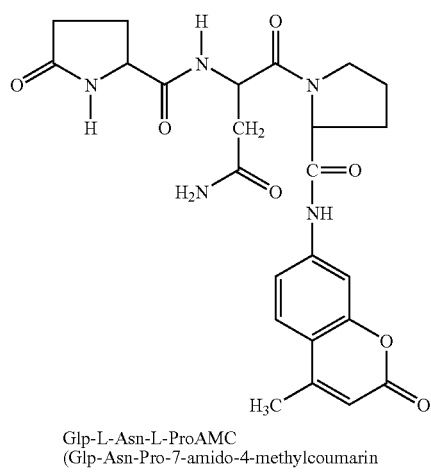
Glp-L-Asn-L-ProAMC
(Glp-Asn-Pro-7-amido-4-methylcoumarin
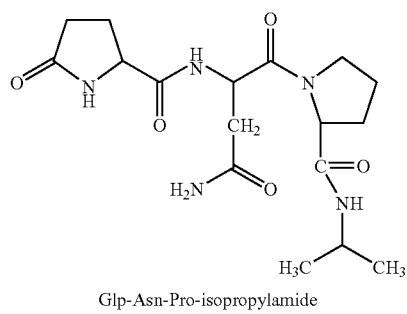
Glp-Asn-Pro-isopropylamide
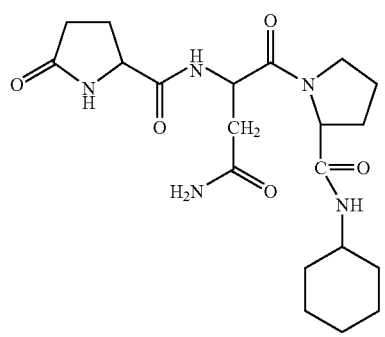
Glp-Asn-Pro-cyclohexamide
-continued
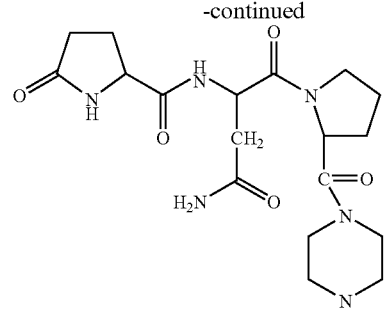
Glp-Asn-Pro-piperazide
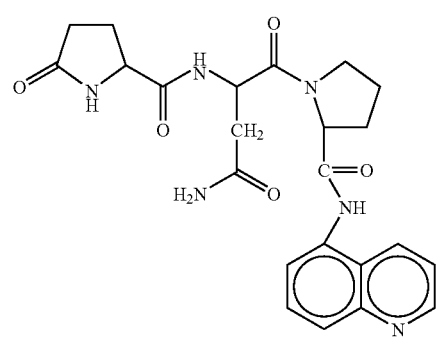
Glp-Asn-Pro-5amidoquinoline
(or 6amidoquinoline or 8amidoquinoline)
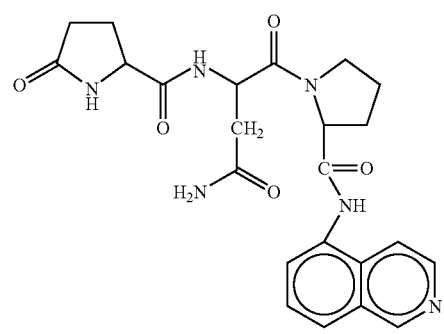
Glp-Asn-Pro-5-amido-isoquinoline
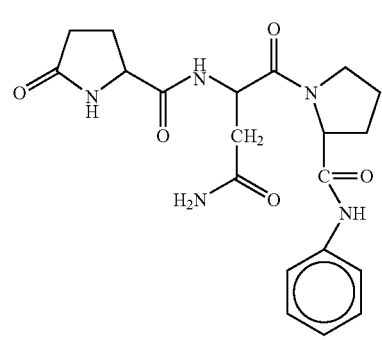
Glp-Asn-Pro-Anilide -continued
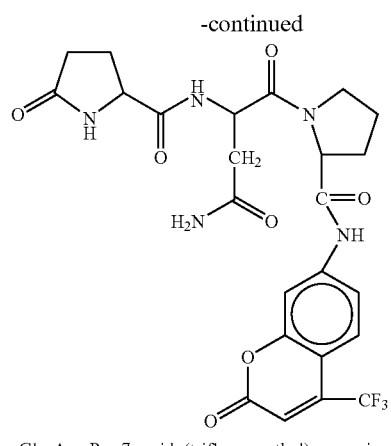
Glp-Asn-Pro-7-amido(trifluoromethyl)coumarin
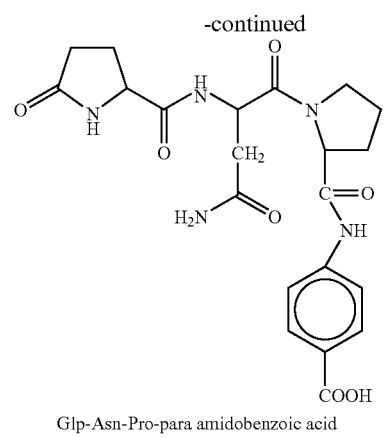
Glp-Asn-Pro-para amidobenzoic acid
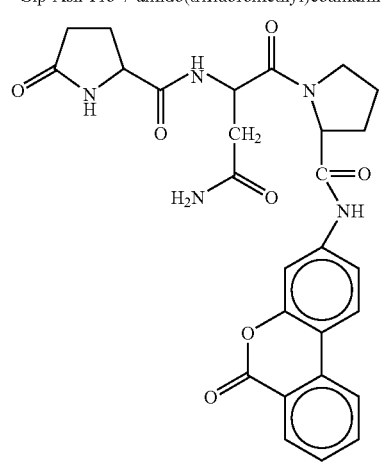
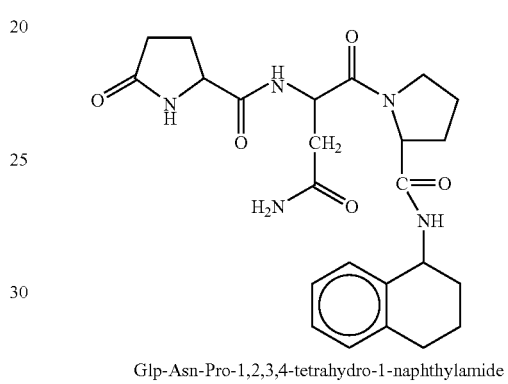
Glp-Asn-Pro-1,2,3,4-tetrahydro-1-naphthylamide
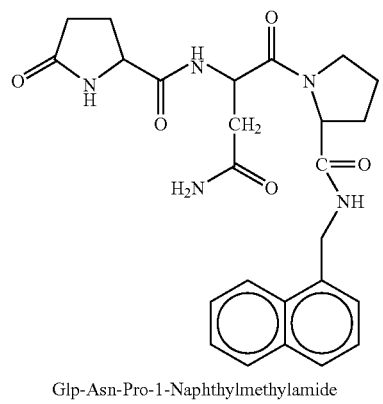
Glp-Asn-Pro-1-Naphthylmethylamide
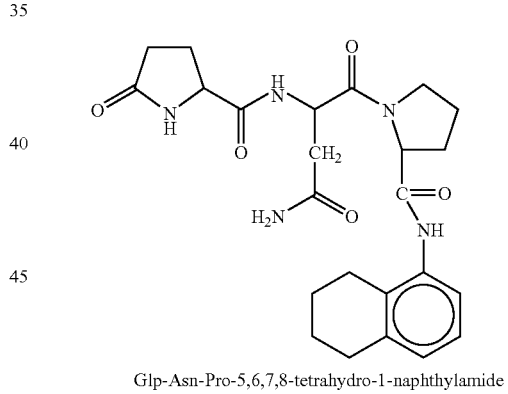
Glp-Asn-Pro-5,6,7,8-tetrahydro-1-naphthylamide
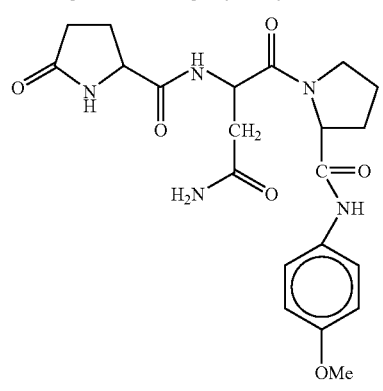
Glp-Asn-Pro-p-Anisidide (-p-methoxyanilide)
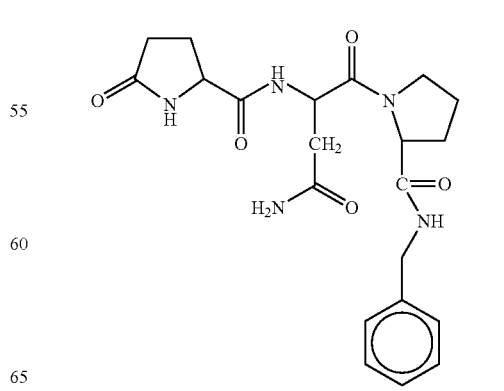
Glp-Asn-Pro-benzylamide -continued

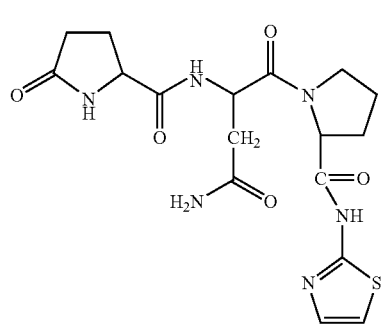

Glp-Asn-Pro-2-thiazolamide

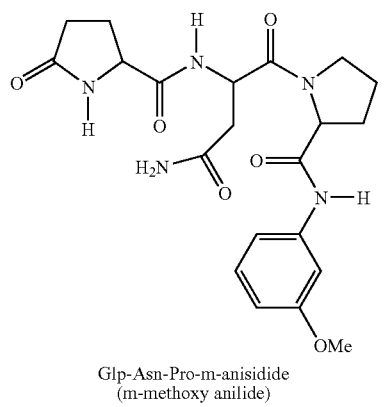

Glp-Asn-Pro-m-anisidide
(m-methoxy anilide)

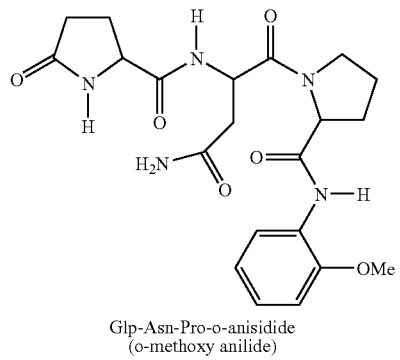

Glp-Asn-Pro-o-anisidide
(o-methoxy anilide)

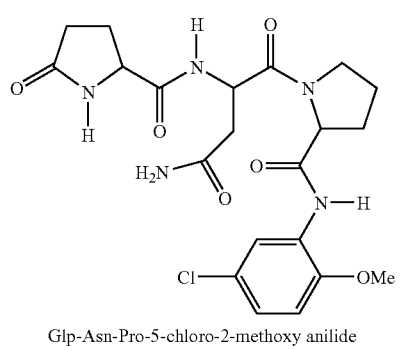

Glp-Asn-Pro-5-chloro-2-methoxy anilide

-continued

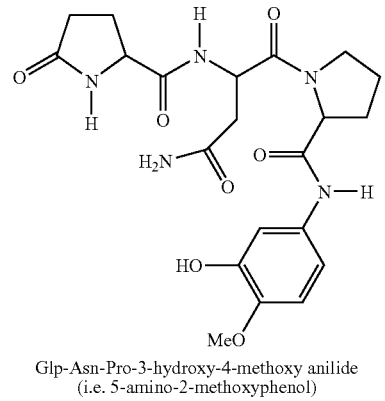

Glp-Asn-Pro-3-hydroxy-4-methoxy anilide
(i.e. 5-amino-2-methoxyphenol)

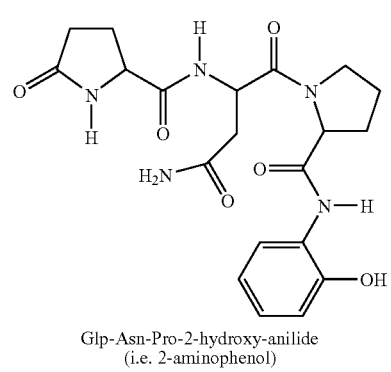

Glp-Asn-Pro-2-hydroxy-anilide
(i.e. 2-aminophenol)

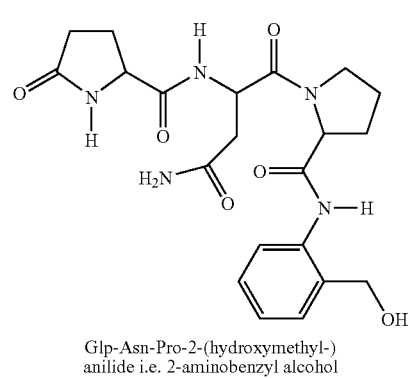

Glp-Asn-Pro-2-(hydroxymethyl-)
anilide i.e. 2-aminobenzyl alcohol

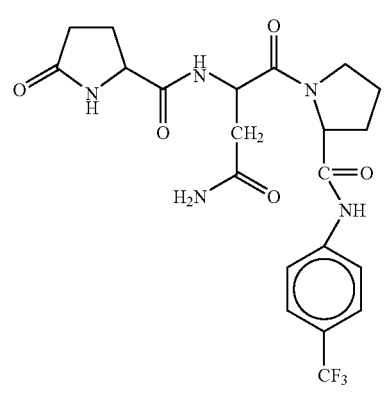

Glp-Asn-Pro-4-trifluoromethyl anilide

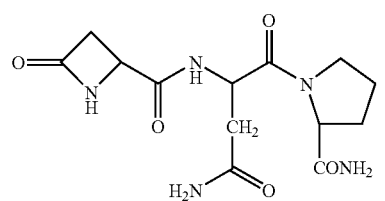
(S)-(-)-4-oxo-2-azetidyl asparaginyl prolineamide
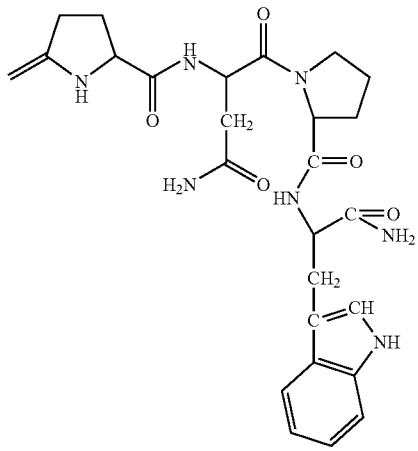
Glp-L-Asn-L-Pro-L-TrpNH$_2$
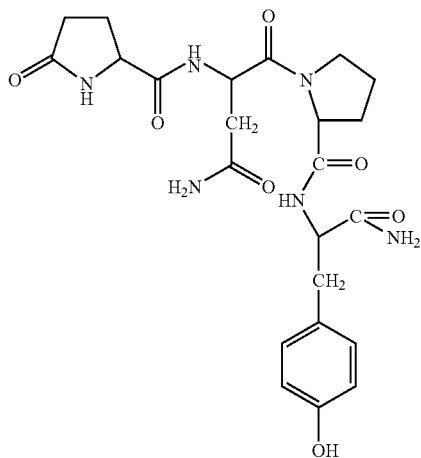
Glp-L-Asn-L-Pro-L-TyrNH$_2$
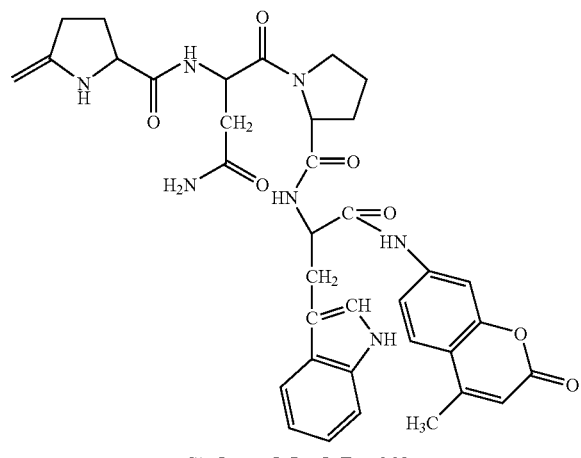
Glp-L-Asn-L-Pro-L-TrpAMC
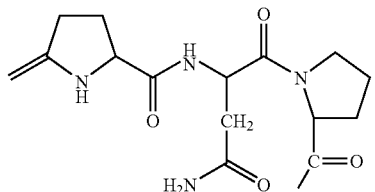
Glp-L-Asn-L-Pro-L-Tyr-L-TrpNH$_2$
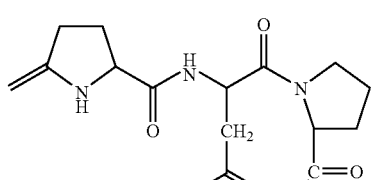
Glp-L-Asn-L-Pro-L-Trp-L-TyrNH$_2$
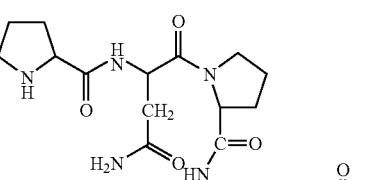
Glp-L-Asn-L-Pro-L-Tyr-L-TrpAMC -continued
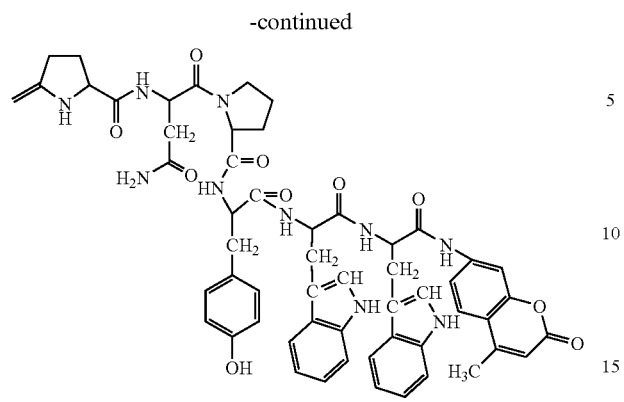
Glp-L-Asn-L-Pro-L-Tyr-L-Trp-L-TrpAMC
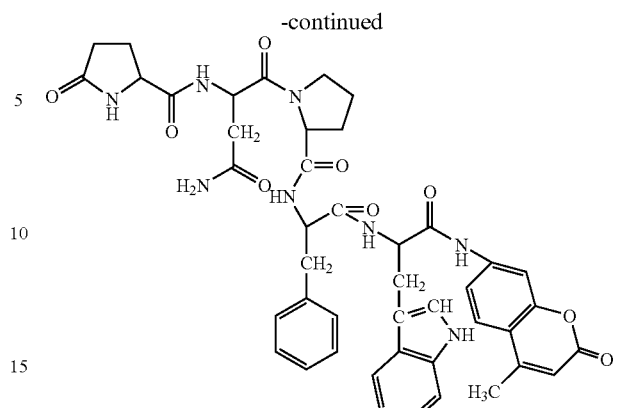
Glp-L-Asn-L-Pro-L-Phe-L-TrpAMC
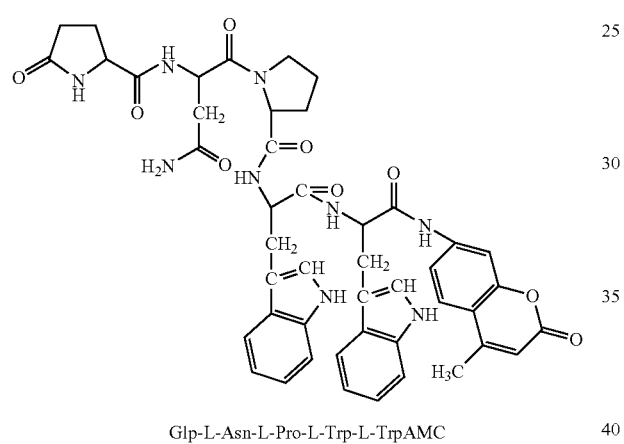
Glp-L-Asn-L-Pro-L-Trp-L-TrpAMC
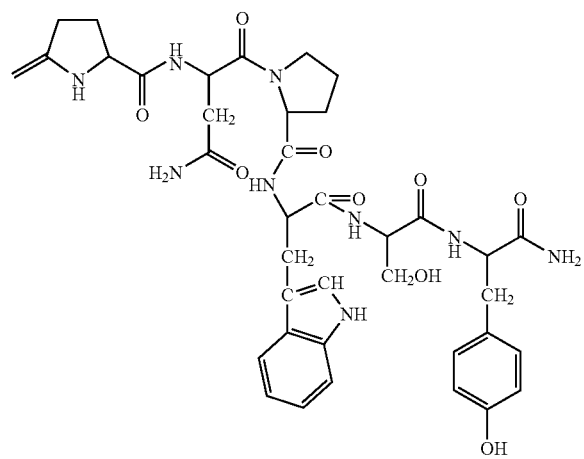
Glp-L-Asn-L-Pro-L-Ala-L-TrpAMC
Glp-L-Asn-L-Pro-L-Trp-L-Ser-L-TyrNH₂
Glp-L-Asn-L-Pro-L-Val-L-Tyr-L-TrpAMC

DETAILED DESCRIPTION OF THE INVENTION

To investigate the influence of $P_1'$ (see Ref. 27) residues on ligand binding to and catalytic activity of TRH-DE, kinetic studies were conducted on a library of 25 peptides in which the central histidine residue of TRH was replaced by a series of other amino acids. Kinetic parameters for the library peptides were measured either by continuous or discontinuous fluorometric assays (23) or by a quantitative HPLC assay (28). All of the assays were developed in the inventor's laboratory and were published recently (23,28). The data collected in this investigation represent the first comprehensive structure-activity study for TRH-DE and the first description of TRH-DE specificity at the $P_1'$ residue.

The abbreviations used are: TRH-DE, Thyrotropin-releasing hormone-degrading ectoenzyme; CNS, central nervous system; TRH, thyrotropin-releasing hormone; Cbz, Benzyloxycarbonyl; βNA, β-naphthylamide; AMC, 7-amino-4-methyl coumarin; TRHAMC, pyroglutamyl-histidyl-prolylamido-4-methyl coumarin; Fmoc, 9-fluoromethyloxycarbonyl; tBu, t-butyl ether; Trt, triphenylmethyl; Pmc, 2,2,5,7,8-pentamethylchromane-6-sulfonyl; Boc, N-α-t-butyloxycarbonyl; OtBu, t-butylester; HPLC, high pressure liquid chromatography; BSA, bovine serum albumin; MBHA, 4-methylbenzylhydrylamine; DMF, N,N-Dimethylformamide; HBTU, 2-(1H-benztriazole-1-yl)-1,1,3,3-tetramethyluronium hexafluorophospahate; HOBt, N-hydroxybenzotriazole; DIPEA, N,N-diisopropylethylamine; DCM, dichloromethane; TFA, trifluoroacetic acid; EDT, 1,2-ethanedithiol; DPP-IV, Dipeptidyl peptidase IV; His-ProDKP, His-Pro diketopiperazine; Glp, pyroglutamic acid; Thi, thienylalanine; RT, retention time; DTT, dithiothreitol; ACN, acetonitrile; Boc, butoxycarbonyl; BOP, benzotriazole-1-yl-oxy-tris(dimethylamino)-phosphonium hexafluorophosphate. All amino acids are in the L-configuration unless otherwise stated.

i.p.=intraperitoneal, i.c.v.=intra-cerebroventricular, min=minutes, s=seconds.

The structures of non-standard amino acids used in the construction of the peptide library are shown below:

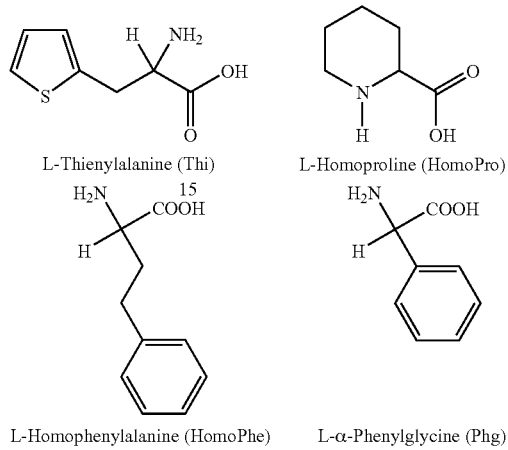

PURIFICATION OF ENZYNES USED IN THE STUDY

Figure 1:
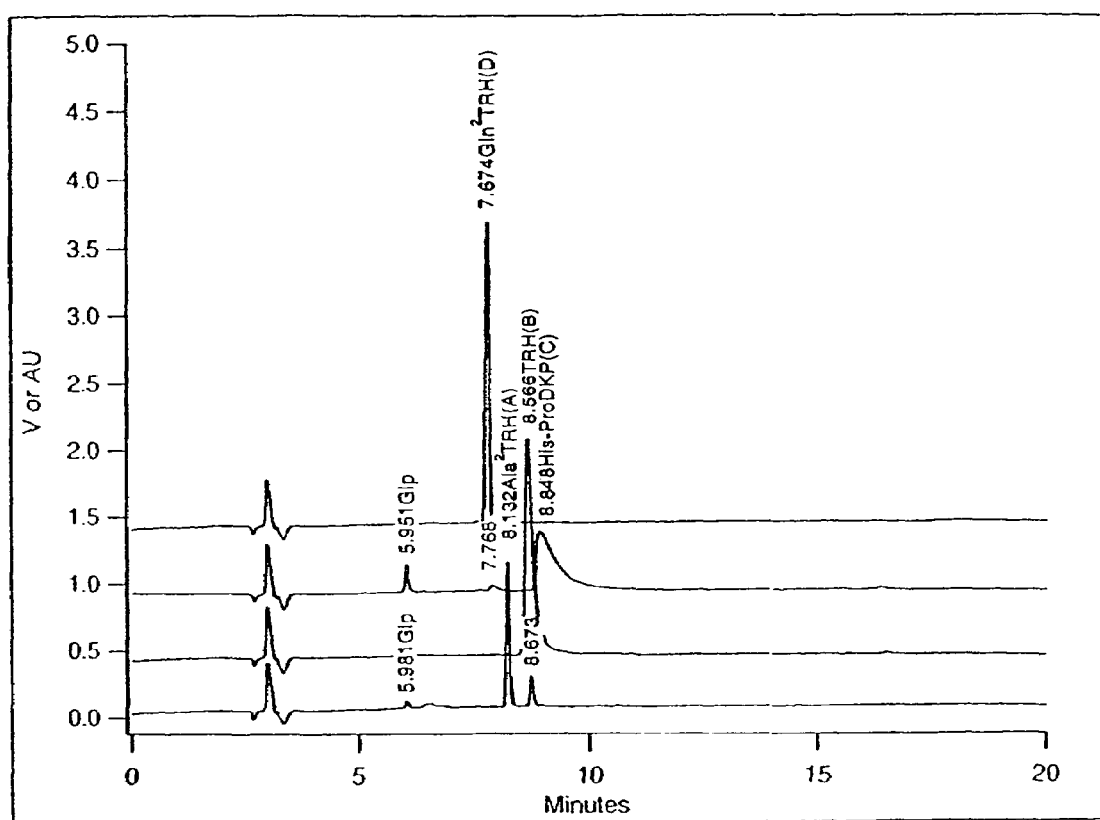
FIG. 1. HPLC traces obtained following the incubation (18 h) of representative library peptides with TRH-DE. Trace B represents the control sample for TRH. In trace C the products formed from TRH by the action of TRH-DE are shown and it can be seen that no TRH (RT 8.566 min) remained. In contrast, poor substrates, such as Glp-Ala-ProNH$_2$ (Ala$^2$TRH), shown in trace A, were not completely degraded under these conditions and the amount of Gip produced was small in comparison to that formed from TRH. Other library peptides, for example Glp-Gln-ProNH$_2$ (Gln$^2$TRH), were not hydrolyzed at all. Thus, in trace D, which depicts a sample of Gln$^2$TRH incubated for 18 h with TRH-DE, there was no evidence of Glp.

The inventor purified TRH-DE from porcine brain according to purification procedures previously published by Dr. K. Bauer, (Max-Planck-Institut, Hannover, Germany) (1). TRH-DE was purified almost 20,000 fold. The preparation was free of other TRH-degrading enzyme activities and was found to have a protein concentration of 0.8 mg ml$^{-1}$ using a modification of the Lowry method with BSA as a standard. This preparation had a specific activity of 0.17 U mg$^{-1}$ with pyroglutamyl-histidyl-prolylamido-4-methyl coumarin (TRHAMC) as substrate under standard conditions of a continuous assay (23). Dipeptidyl peptidase IV (DPP-IV) (EC 3.4.14.5), purified from bovine kidney (7.7 mg ml$^{-1}$, specific activity of 17.5 U mg$^{-1}$ with Gly-ProAMC as substrate), was obtained as a gilt from Dr. C. H. Williams (Queen's University Belfast, U.K). (DPP-IV was used as the coupling enzyme used in the fluorometric assays).

One unit (U) of enzyme activity was defined as that amount catalysing the formation of one µmol of product in one minute under the standard conditions employed. All incubations in the assays described below were carried out in 20 mM potassium phosphate buffer, pH 7.5, at 37° C.

Standard Preparation of the Compounds of the Invention and Comparative Compounds Compounds of the invention may be prepared by standard Fmoc peptide chemistry (29). Of the 25 library peptides studied, Glp-His-ProNH$_2$, Glp-Glu-ProNH$_2$ and Glp-His-ProOH were purchased from Sigma-Aldrich (Ireland). Glp-Gln-ProNH$_2$, Glp-Phe-ProNH$_2$ and Glp-Asn-Pro-AMC were bought from Peninsula Laboratories Inc., (UK). Glp-Asn-ProNH$_2$, Glp-Tyr-ProNH$_2$ and Glp-D-Asn-ProNH$_2$ were custom synthesised by the American Peptide Company (Sunnyvale, Calif., U.S.A.) at the request of the inventor under conditions of confidentiality, in addition to being synthesised by the method described below. All other peptides in the library were synthesised either manually using a bubbler system (for details, see Ref. 29) or using a Synergy Peptide Synthesiser (Applied Biosystems, UK). In both cases, standard solid-phase Fmoc chemistry was employed (29). Pyroglutamic acid and Fmoc amino acid derivatives were purchased from Calbiochem-Novabiochem UK Ltd. Tri-functional amino acids were obtained with side-chain protecting groups as follows: Fmoc-Ser(tBu)-OH, Fmoc-Thr(tBu)-OH, Fmoc-Asn(Trt)-OH, Fmoc-D-Asn(Trt)-OH, Fmoc-Arg(Pmc)-OH, Fmoc-Lys(Boc)-OH, Fmoc-Asp(OtBu)-OH, Fmoc-His(Trt)-OH, and Fmoc-Cys(Trt)-OH. In general, synthesis was carried out on Rink amide MBHA resin (Calbiochem-Novabiochem UK Ltd.) with a loading capacity 0.64 mmol gm$^{-1}$. The resin was swollen using DMF and deprotected with 20% piperidine in DMF. Coupling was performed twice for each amino acid using the Synergy Peptide Synthesizer and once when the bubbler system was employed. Three equivalents (i.e. 3-fold excess over the resin loading capacity) of each amino acid were coupled onto the resin with HBTU/HOBt/DIPEA (1:1:2 equivalents) at each step. No deprotection step was necessary after the coupling of pyroglutamic acid. On completion of peptide assembly, the resin was washed thoroughly with DCM followed by methanol and allowed to dry overnight. In the absence of labile amino acids and side-protection groups, cleavage of the peptide from the resin was achieved by placing the dry resin in a round-bottomed flask and adding 95% (v/v) TFA in water (10 ml per 1 gm dry resin). This reaction mixture was stirred at room temperature for approximately one hour before filtering the suspension through a sintered glass funnel. Sequences containing Asn were deprotected and cleaved using a TFA solution containing 95% TFA, 2.5% water and 2.5% triisopropylsilane (v/v/v). For sequences containing serine, tryptophan or arginine, cleavage/deprotection was achieved using Reagent K (82.5% TFA/5% water/5% thioanisole/5% phenol/2.5% EDT, v/v/v/v/v) in place of TFA (28, 29).

These small peptides proved difficult to precipitate directly from the filtrate using diethyl ether, so the TFA and scavengers were first removed by rotary evaporation. The residue was washed with petroleum ether and diethyl ether was then added to precipitate the peptide. A steady stream of nitrogen was used to evaporate the diethyl ether and dry the peptide pellet simultaneously. Because of the hygroscopic nature of these peptides, it was essential to dry the peptide pellets thoroughly under nitrogen before transferring them to glass containers for storage in a dessicator at −20° C.

Glp-Asn-ProAMC was custom synthesised by the American Peptide Company (Sunnyvale, Calif., U.S.A) at the request of the inventor under conditions of confidentiality.

EXAMPLE I

Preparation of Exemplary Compound used in the Invention: Glp-Asn-ProNH$_2$

Synthesis of the title compound was carried out using a manual bubbler system incorporating a scintered glass funnel with a capacity of approximately 150 ml and a three-way tap system as described in the Catalogue & Peptide Synthesis Handbook supplied by Calbiochem-Novabiochem UK Ltd. 2 g of MBHA Rink amide resin (Calbiochem-Novabiochem UK Ltd.) with a loading capacity of 0.55 mmol/gm were weighed out and transferred to the bubbler system. (Note the loading capacity of the resin varied slightly with each batch). The resin was swelled in approximately 20 ml of DMF for 10 min and deprotected using 20% piperidine in DMF for 60 min. The resin was then washed three times with DMF and a Kaiser-ninhydrin test was performed on a small quantity of the resin to ensure complete deprotection had occurred. 1.11 g of Fmoc-Pro-OH were dissolved in 20 ml DMF and to this solution 1.25 g of HBTU and 0.5 g of HOBt were added and mixed. 1.23 ml of DIPEA was then added to the mixture. This activated amino acid derivative was then added to the deprotected resin and coupling was allowed to proceed for 60 min. After this time the resin was drained and washed 3 times with DMF and the Kaiser-ninhydrin test was repeated. The resin bound fmoc-Pro was then deprotected using 20% piperidine in DMF for one hour. The resin was again drained and washed 3 times with DMF. 1.96 g of fmoc-Asn(Trt)-OH were dissolved in 20 ml DMF. This second amino acid was then coupled to the resin and deprotected as described above. A Kaiser-ninhydrin test was carried out to ensure complete deprotection of the Asn residue had occurred before coupling the final Glp residue. 0.42 g of Pyr-OH (Glp) was dissolved in 20 ml of DMF and coupled to the resin as described above. No deprotection was necessary after the coupling of Glp. The resin was then washed 3 times with DMF, 3 times with DCM and 3 times with methanol before being allowed to dry overnight. The following day, the resin was placed in a 100 ml round-bottomed flask to which was added 20 ml of a TFA solution containing 95% TFA, 2.5% water, and 2.5% triisopropylsilane. The flask was stoppered and cleavage of the peptide from the resin was allowed to proceed for 60 min at room temperature with constant stirring. The resin was removed by filtration under reduced pressure and washed twice with the TFA solution. The TFA and scavenger were removed by rotary evaporation. The residue was washed with petroleum ether and diethyl ether was added to precipitate the peptide. Excess diethyl ether was removed by pipette. A steady stream of nitrogen was used to evaporate off the remaining diethyl ether and to thoroughly dry the peptide pellet. The peptide was then transferred to a glass container for storage in a dessicator at −20° C. HPLC analysis of a 1 mM solution of the peptide in 20 mM potassium phosphate buffer pH 7.5 was conducted as described in Table I.

Preparation of Glp-Asn-Pro-NH$_2$ by American Peptide Company $C_{14}H_{21}N_5O_5$ MVW 339.4

Peptide Preparation Process

The synthesis is performed by incorporating the c-terminal end of the amino acid to an amino group in an appropriate support, MBHA resin. The peptide chain is then formed by coupling the C-terminal of another amino acid to the N-terminal of the previous amino acid that was previously coupled to the solid support. American Peptide Company provides Boc amino acids and resin. Biograde DCM, DMF and related solvents are obtained from Fisher Scientific.

Boc-Pro; Boc-Asn; Glp; HBTU and MBHA resin x g of peptide resin was transferred into a ~x ml size cleavage vessel. HF was filled in and a low-high HF cleavage was conducted. After the HF cleavage, extract the CAN/H$_2$O. Crude peptide is purified with RP-HPLC.

Preparative HPLC, Shimadzu 8-LC
Analytical HPLC Shimadzu 10-LC
Analytical column YMC 5 micron C18
Preparative column 3 inch Varian 10 micron C18 RP-HPLC Collect those fraction >95. Dry it over Virtis lyophilizer and white powder was obtained with good yield. The material was finally tested and release by QC with that parameter specified in COA.

Glp-Asn-Pro-NH$_2$ prepared by this process exhibited the correct molecular weight in Mass Spectral analysis (MALDI-TOF). It had a solubility of 1 mg/ml in water.

RP-HPLC Analysis

| | | | |
|---|---|---|---|
| Column | Vydac C18 5u | | |
| Flow rate: | 1.0 ml/min | Gradient type: | Linear |
| Buffer A: | 0.1% TFA in H$_2$O | Buffer B: | 0.1% TFA in Acetonitrile |
| From | 0% | To  10% | During  20 min |
| Wavelength | 215 nm | Sens  0.16 | Paper Speed  5 mm/min |
| Retention Time | 10.627 min | | |

Preparation of Glp-Asn-ProAMC by American Peptide Company $C_{24}H_{27}N_5O_7$ MW 497.5

Peptide Preparation Process

This peptide was prepared by solution phase chemistry. American Peptide Company provides Boc amino acids and resin. Biograde DCM, DMF and related solvents were obtained from Fisher Scientific.

Boc-Pro; Boc-Asn; Glp; BOP and AMC x g of AMC was dissolved in DMF. The BOP reagent and Boc-Pro were added to the reaction mixture for a period of two hours. Let the reaction react for ~2 hours. Use standard work-up procedure to generate Boc-ProAMC analog.

Following removal of Boc group of Boc-ProAMC, Boc-Asn was added along with coupling agent. Noc-Asn-ProAMC was obtained. Repeat same process, Glp was coupled to the sequence. Since no protection was employed, HF cleavage step was avoided. However, if Boc-Asn(Xan) had been used, HF step would have been necessary. After the HF cleavage, extract the ACN/H$_2$O. Crude peptide is purified with RP-HPLC.

Preparative HPLC, Shimadzu 8-LC
Analytical HPLC Shimadzu 10-LC
Analytical column YMC 5 micron C18
Preparative column 3 inch Varian 10 micron C18 RP-HPLC Collect those fraction >95. Dry it over Virtis lyophilizer and white powder was obtained with good yield. The material was finally tested and released by QC with that parameter specified in COA. Glp-Asn-ProAMC prepared by this process exhibited the correct molecular weight in Mass Spectral analysis. It had a solubility of 0.5 mg in 0.5 ml water.

RP-HPLC Analysis

| | |
|---|---|
| Column: | 4.6 m i.d. × 250: vydac, c18, 5 micron |
| Others: | F:1.5 ml/min |
| Buffer A: | 0.1% TFA in water Buffer B: 0.1% TFA in ACN |
| Wavelength 215 nm | |
| C:\CLASS-VP\METHODS\5-35% 20 25.met | |
| Retention Time 13.7 min | |

Derivatives of this type have been previously synthesised by well known solution solid phase procedures using Boc chemistry (Zimmerman et al.1977 (30), (Fujiwara & Tsuru, 1978 (31)). Glp-Asn-ProAMC and other compounds of the invention can be prepared utilising such procedures which are readily understood by those of ordinary skill in the art. As such, the above experimental procedure utilised by APC to provide Glp-Asn-ProAMC herein is only exemplary of suitable methods and this should not be considered to limit the present invention.

Preparation of Glp-Asn-Proamides by Solution Phase Chemistry

Carboxamides of the invention may be prepared by standard solution phase coupling chemistry using Glp-Asn-Pro and the appropriate amine. Glp-Asn-Pro was obtained from the American Peptide Company (Sunnyvale, Calif., U.S.A.). 2-Aminobenzyl alcohol, o-anisidine, m-anisidine, p-anisidine, 5-amino-2-methoxyphenol, 2-aminophenol, 1,2,3,4 tetrahydro-1-naphthylamine, 5,6,7,8 tetrahydro-1-naphthylamine, benzylamine, 5-chloro-2-methoxy aniline were purchased from the Sigmna-Aldrich Chemical Company. Glp-Asn-Pro was transferred to a flask equipped with a magnetic stirrer. DMF was introduced followed by the amine, HOBt and DCC (1:1:1 equivalents). The reaction mixture was stirred for 24 hours, filtered, and the solvent evaporated at room temperature. The residue was washed successively with small volumes of ethyl acetate, diethyl ether, and petroleum ether. The amides were further purified by preparative HPLC using a Waters WAE-84176 semi prep C18 HPLC column. Two isomers of the 1,2,3,4-tetrahydro-1-naphthylamide were isolated by HPLC. These were tested separately. (See Tables VI-VII below).

Glp-Asn-Pro-Tyr-NH$_2$, Glp-Asn-Pro-Trp-Ser-Tyr-NH$_2$, Glp-Asn-Pro-Trp-Tyr-NH$_2$, Glp-Asn-Pro-Trp-NH$_2$, Glp-Asn-Pro-Tyr-Trp-NH$_2$, Glp-Asn-Pro-Trp-AMC and Glp- Asn-Pro-Tyr-Trp-AMC were synthesised by PolyPeptide Laboratories GmbH (Germany) at the request of the inventor under conditions of confidentiality, by a combination of standard solid phase Fmoc peptide chemistry and solution phase chemistry. PolyPeptide Laboratories GmbH provided Mass Spectral and HPLC analysis to confirm the identity and purity of the peptides that they supplied.

Analysis of Peptides

All of the library peptides were analysed and judged to be homogeneous by HPLC (see Table I). HPLC analysis was conducted using a Thermo Separation Products Inc., Spectra System HPLC. Standard 1 mM solution of peptide in 20 mM potassium phosphate buffer pH 7.5 was analysed on a C-18 reverse-phase column (Hypersil UK) using a linear gradient of 0-70% acetonitrile in 0.08% TFA as previously described (21). In addition, the American Peptide Company provided Mass Spectral analysis and HPLC analysis to confirm the identity of the peptides synthesised by them. Similarly, Sigma-Aldrich (Ireland) and Peninsula Laboratories Inc., (UK) provided amino acid analysis and HPLC analysis. HPLC traces obtained for peptides synthesised in the laboratory were similar to those obtained for peptides purchased from the Arnerican Peptide Company (Sunnyvale, Calif., U.S.A.).

TABLE I

HPLC Analysis

| Analogue | Synthesised in Inventor's Lab | Synthesised by APC | Synthesised by other companies |
| --- | --- | --- | --- |
| pGlu-His ProOH |  |  | 9.66 |
| pGlu-His-ProNH2 |  |  | 8.68 |
| pGlu-Thi-ProNH2 | 13.70 |  |  |
| pGlu-Phe-ProNH2 |  |  | 14.47 |
| pGlu-Tyr-ProNH2 | 11.50 | 11.35 |  |
| pGlu-Arg-ProNH2 | 9.35 |  |  |
| pGlu-Lys-ProNH2 | 8.41 | 8.38 |  |
| pGlu-norVal-ProNH2 | 11.05 | 11.06 |  |
| pGlu-homoPhe-ProNH2 | 16.62 |  |  |
| pGlu-Ser-ProNH2 | 7.50 | 7.54 |  |
| pGlu-Ala-ProNH2 | 8.13 |  |  |
| pGlu-Thr-ProNH2 | 8.08 |  |  |
| pGlu-Ileu-ProNH2 | 12.47 |  |  |
| pGlu-Met-ProNH2 |  | 11.51 |  |
| pGlu-Leu-ProNH2 | 12.97 | 12.97 |  |
| pGlu-Val-ProNH2 | 10.55 |  |  |
| pGlu-homoPro-ProNH2 | 10.22 |  |  |
| pGlu-Gly-ProNH2 | 7.85 |  |  |
| pGlu-Pro-ProNH2 | 8.70 |  |  |
| pGlu-DAsn-ProNH2 | 7.77 |  |  |
| pGlu-Asn-ProNH2 | 7.53 | 7.43 |  |
| pGlu-Gln-ProNH2 |  |  | 7.73 |
| pGlu-Trp-ProNH2 | 16.12 | 16.13 |  |
| pGlu-Asp-ProNH2 | 7.80 |  |  |
| pGlu-Glu-ProNH2 |  |  | 8.28 |
| pGlu-PheGly-ProNH2 | 12.65 |  |  |

HPLC Analysis of the Peptide Library—Retention Times (Min) are Shown for Each Peptide.

Retention times are compared for peptides synthesised either by the inventor, the American Peptide Company (APC; Sunnyvale, Calif., U.S.A.), or other commercial companies (for details see text above ). HPLC analysis was conducted employing a Thermo Separation Products Spectra System HPLC. Peptides were eluted from a C-18 reverse-phase HPLC column using a linear gradient of 0-70% acetonitrile in 0.08% trifluoroacetic acid over a period of 30 min. UV absorbance was measured at 206 nm.

Kinetic Studies

Kinetic analysis of the peptide library using HPLC—The ability of each peptide in the library to act as a TRH-DE substrate was assessed using HPLC. As an initial screen, 1 mM peptide was incubated with 0.8 μg TRH-DE in a total volume of 1 ml for 18 h at 37° C. Control samples were included in which peptide (1 mM) or Glp (0.2 mM-0.8 mM) were incubated under identical conditions in the absence of TRH-DE. TRH-DE activity was terminated by the addition of TFA (0.15% v/v) and samples were then analysed using HPLC as described previously (24). Products resulting from TRH-DE hydrolysis could be separated on a C-18 reverse-phase column (Hypersil, UK) using a linear gradient of 0-70% acetonitrile in 0.08% (v/v) TFA. The concentration of Glp formed by the action of TRH-DE on the peptide library was measured by UV absorbance at 206 nm with a quantitative detection limit of 0.1 mM for a 40 μl injection volume, employing a signal to noise ratio of 10. Following the incubation of each peptide with TRH-DE, evidence of Glp in the sample was taken to indicate that the peptide was a TRH-DE substrate.

The rates of hydrolysis for each of those peptides identified as substrates were then compared by measuring Gip production using microassays with shorter incubation times. In these assays peptide (1 mM) was incubated at 37° C. in a total volume of 100 μl. 0.8-3.2 μg TRH-DE and incubation times of 5 min to 18 h were used routinely. Measurements were made in triplicate. The rate of TRH-OH hydrolysis was also measured by this method.

Determination of inhibitor constants for selected TRH-DE substrates—The HPLC assay lacked sufficient sensitivity for determining kinetic constants. Therefore, those peptides undergoing significant hydrolysis (i.e. those that exhibited rates of hydrolysis $\geq 0.5$ U mg$^{-1}$) were examined as competitive substrates of TRH-DE, using a recently published discontinuous fluorometric TRH-DE assay (23). This assay employs TRHAMC as the substrate and depends on the measurement of the fluorescence of 7-amino-4 methyl coumarin (AMC) produced as follows:

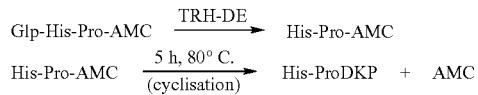

We have shown that the amount of AMC formed under these conditions is a quantitative measure of TRHAMC cleavage (23). Initial rates for the hydrolysis of TRHAMC by TRH-DE were determined in triplicate at five different substrate concentrations both in the absence and presence of at least three concentrations of peptide. $K_i$ values were obtained by non-linear regression analysis of the data collected. Determined in this way (i.e. by treating the peptide substrates as inhibitors of TRHAMC hydrolysis), these $K_i$ values correspond to the Michaelis constants for those library peptides hydrolysed by TRH-DE (32).

Kinetic analysis of peptides that are not hydrolysed by TRH-DE. A recently-developed continuous coupled fluorometric assay (23) was used to investigate the ability of those library peptides that were not hydrolysed by TRH-DE to inhibit TRHAMC degradation by TRH-DE. In this assay, TRHAMC is the substrate and dipeptidyl peptidase IV (DPP-IV) (EC 3.4.14.5) is the coupling enzyme. The reaction sequence is:

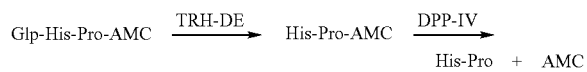

The reaction was monitored continuously by measuring the increase in AMC fluorescence. A linear progress curve with no discernible lag period was observed when the reaction was monitored over a period of 10 minutes. Nevertheless, data sampling was not commenced until 100 s from the start of the reaction to ensure measurements were taken after a steady state had been reached (see Ref. 23).

In a preliminary experiment, the peptides were screened for their ability to inhibit TRH-DE activity. The initial rate of TRHAMC hydrolysis by TRH-DE was measured by incubating 5 µM TRHAMC with 1.23 µg DPP-IV and 0.32 µg TRH-DE, both in the absence and presence of each library peptide (1 mM final concentration) under standard assay conditions (23). In each case the percentage inhibition ($i_{\%}$) was calculated using the equation $i_{\%}=100(1-v_i/v_o)$, where $v_i$ and $v_o$ are the initial velocities in the presence and absence of peptide, respectively.

$K_i$ values for peptides giving <20% inhibition, under these conditions, were calculated to be greater than 1 mM using the relationship for competitive inhibition $i=[I]/\{[I]+K_i(1+[S]/K_m)\}$ where i is the fractional amount of inhibition observed, [I] is the concentration of the peptide, [S] is the concentration of substrate and $K_m$ is the Michaelis constant for TRHAMC, which was found to be 3.5±0.4 µM (n=6) (see below). Since these peptides were poor inhibitors they were not examined further. The $K_i$ values for the remainder of the peptides were determined by measuring their effects on TRHAMC degradation by TRH-DE using the continuous assay. Data were collected in duplicate at five different substrate concentrations and at least three different concentrations of each peptide.

All peptides that were observed to inhibit AMC production in the continuous coupled assay were assessed for their ability to inhibit the coupling enzyme, DPP-IV, using a direct continuous assay for DPP-IV that employed Gly-ProAMC as the substrate (23). Peptide concentrations similar to those used to determine the $K_i$ values above were employed in the DPP-IV assay. None of these peptides were found to inhibit DPP-IV hydrolysis of Gly-ProAMC. Thus, the effects produced by the peptides can be attributed solely to their inhibition of TRH-DE.

Reversibility and time dependence of the inhibition produced by Glp-Gln-ProNH$_2$, Glp-Asn-ProNH$_2$ and Glp-Asn-ProAMC were examined by initially preincubating TRH-DE with each peptide at 37° C. for various periods up to 75 min. To investigate time dependence, the enzyme-peptide solution was subsequently added to the reaction mixture containing TRHAMC, DPP-IV, buffer and peptide, and TRH-DE activity was measured using the continuous assay. The final concentration of Glp-Gln-ProNH$_2$, Glp-Asn-ProNH$_2$ and Glp-Asn-ProAMC used was 400, 160 and 1 µM, respectively. To test for reversibility, the enzyme-peptide solution was added to a reaction mixture that did not contain peptide. TRH-DE activity was not affected by pre-incubation at 37° C.

Fluorescence measurements were made using a Perkin Elmer LS 50B Luminescence Spectrometer fitted with a thermostated cell holder. Wavelengths for excitation and emission were set at 370 nm and 440 nm, respectively, with slit widths of 10 nm and 5 nm, respectively.

Analyses of results. All kinetic parameters were determined by non-linear regression analysis using the computer program Prism (Graph Pad Software Inc. U.S.A). Linear regression analysis employing proportional weighting was used to fit data to linear plots for display purposes only. Unless otherwise stated, all values are shown as the mean±SD.

RESULTS

HPLC analysis of the peptide library. HPLC analysis revealed that TRH-DE catalyzed the removal of the N-terminal Glp residue from 15 out of the 25 members of the peptide library, including TRH. It can be seen from the representative HPLC traces shown in FIG. 1 that following overnight incubation with TRH-DE, 1 mM Glp-His-ProNH$_2$ (TRH) was degraded fully. In contrast, Glp-Ala-ProNH$_2$ was only partially degraded to produce a relatively small amount of Glp (0.2 mM). No detectable Glp was released from Glp-Gln-ProNH$_2$ (FIG. 1) or from those peptides where the P$_1$' position was occupied by D-Asn, Gly or the L-amino acids Asn, Trp, Phg, HomoPro, Glu, Asp, and Pro (not shown). The HPLC-based assay also showed that there was no detectable cleavage of Glp-Cys-ProNH$_2$ by TRH-DE. This peptide, however, was observed to undergo oxidation with disulfide bond formation during incubation and it was not examined further. Table II shows the rates of hydrolysis of those peptides that were found to be substrates for TRH-DE.

Figure 2:
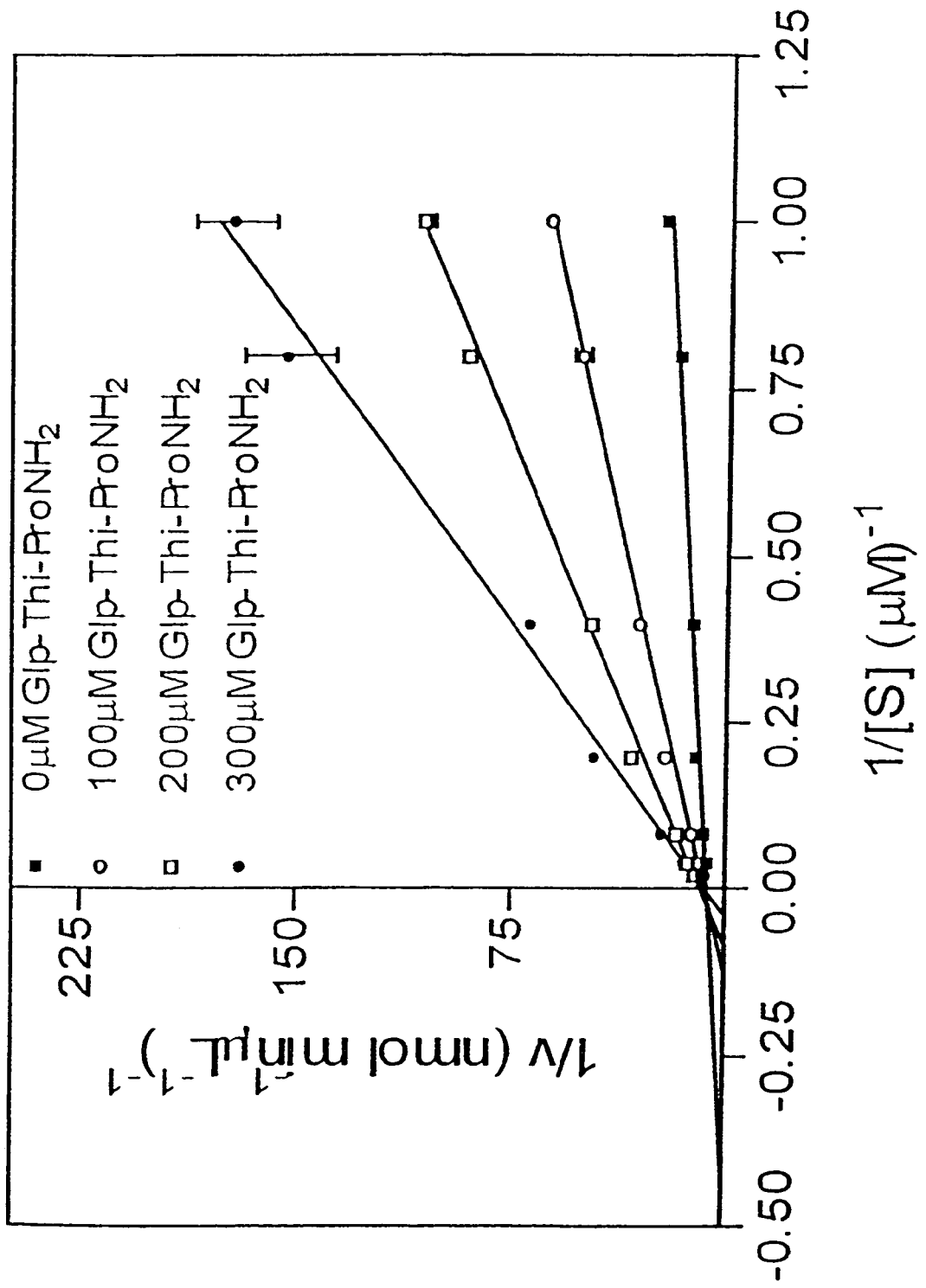
FIG. 2. Lineweaver-Burk plot for TRHAMC degradation by TRH-DE in the presence of increasing concentrations of Glp-Thi-ProNH$_2$. Data were obtained using the discontinuous fluorometric assay and represent the mean±SEM (n=3). Error bars can be seen where the SEM is greater than the size of the symbol.

Inhibitor constants for selected TRH-DE substrates. $K_i$ values for those library peptides that were significantly hydrolyzed by TRH-DE are shown in Table III. All of these peptides were found to act as simple competitive inhibitors of the degradation of TRHAMC by TRH-DE (example shown in FIG. 2). Non-linear regression analysis of the data collected in this study gave a $K_m$ value for TRHAMC of 3.1±0.5 µM (n=8). $V_{max}/K_m$ values (Table II) were calculated assuming that the $K_i$ values for these peptides correspond to Michaelis constants (33).

Figure 3:
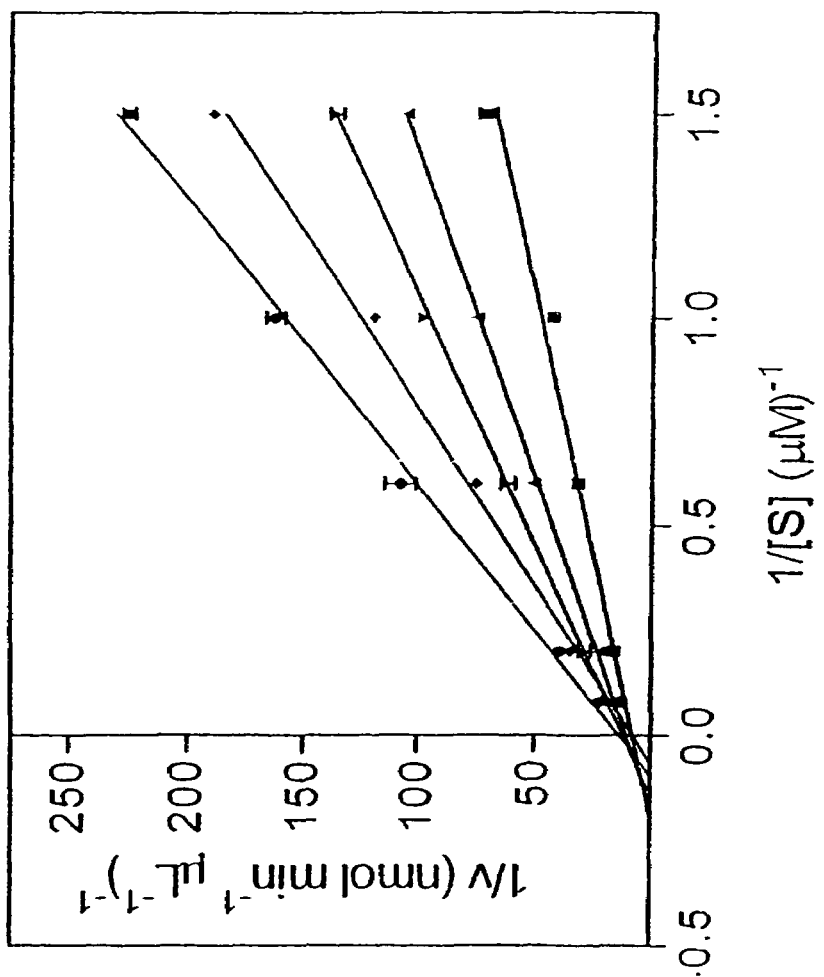
FIG. 3. Lineweaver-Burk plot for inhibition of TRH-DE hydrolysis of TRHAMC by Glp-Asn-ProNH$_2$. Initial rates were determined using the continuous fluorometric assay. Data are shown as a Lineweaver-Burk plot for illustrative purposes and represent the mean±SEM (3). Error bars can be seen where the SEM is greater than the size of the symbol.

Kinetic Analysis of peptides not hydrolyzed by TRH-DE. As noted above, 15 out of the 25 members of the peptide library, including TRH, were found to be TRH-DE substrates. Only one of these peptides, Glp-Tyr-ProNH$_2$, displayed a $K_m$ value that was lower than that of TRH. Of the remaining 10 peptides that were not hydrolysed by TRH-DE, 5 were found to inhibit TRH-DE with $K_i$ values of <1000 µM. Of these, only one, Glp-Asn-ProNH$_2$, was found to display a binding affinity greater than TRH. Table IV shows the percent inhibition of TRH-DE by each of the enzyme-resistant peptides measured by the continuous coupled assay under standard conditions. Also presented are the $K_i$ values obtained for those peptides exhibiting greater than 20% inhibition in the initial screening. The latter peptides were all found to act in a simple competitive manner, as illustrated by a Lineweaver-Burk plot of data obtained for Glp-Asn-ProNH$_2$ (FIG. 3). Inhibition by Glp-Gln-ProN-H$_2$, Glp-Asn-ProNH$_2$ and Glp-Asn-ProAMC was found to be fully reversible and not time-dependent. Non-linear regression analysis of data from the continuous assay gave a $K_m$ value of 3.5±0.4 µM (n=6) for TRHAMC.

TABLE II

| Peptide | Rate of hydrolysis (U mg$^{-1}$) |
| --- | --- |
| Glp-His-ProOH | 3.38 ± 0.18 (3) |
| Glp-His-ProNH$_2$ | 2.54 ± 0.25 (11) |
| Glp-Thi-ProNH$_2$ | 2.12 ± 0.16 (6) |
| Glp-Phe-ProNH$_2$ | 1.56 ± 0.13 (5) |
| Glp-Tyr-ProNH$_2$ | 0.66 ± 0.04 (5) |
| Glp-Arg-ProNH$_2$ | 0.41 ± 0.02 (4) |
| Glp-Lys-ProNH$_2$ | 0.46 ± 0.02 (3) |
| Glp-Met-ProNH$_2$ | 0.21 ± 0.03 (4) |
| Glp-Leu-ProNH$_2$ | 0.14 ± 0.01 (5) |
| Glp-Thr-ProNH$_2$ | 0.14 ± 0.01 (5) |
| Glp-Ileu-ProNH$_2$ | 0.06 ± 0.00 (4) |
| Glp-homoPhe-ProNH$_2$ | 0.05 ± 0.00 (3) |
| Glp-Val-ProNH$_2$ | 0.05 ± 0.00 (3) |
| Glp-Ser-ProNH$_2$ | 0.05 ± 0.00 (3) |
| Glp-NorVal-ProNH$_2$ | 0.04 ± 0.00 (6) |
| Glp-Ala-ProNH$_2$ | 0.02 ± 0.00 (3) |

Comparison of hydrolysis rates for library peptides (1 mM) found to be TRH-DE substrates. Rates of hydrolysis were determined as outlined under "Experimental Procedures" Each value represents the mean±S.D. The number of determinations is indicated in brackets.

TABLE III

| Peptide | V$_{max}$ (U mg$^{-1}$) | K$_m$ (μM) | V$_{max}$/K$_m$ (U mg$^{-1}$ μM$^{-1}$) |
| --- | --- | --- | --- |
| Glp-His-ProNH$_2$ | 2.63 ± 0.26 (11) | *35 ± 4 (3) | 0.08 ± 0.01 |
| Glp-Thi-ProNH$_2$ | 2.19 ± 0.16 (6) | 34 ± 6 (3) | 0.06 ± 0.01 |
| Glp-Tyr-ProNH$_2$ | 0.67 ± 0.04 (5) | 15 ± 3 (4) | 0.05 ± 0.01 |
| Glp-His-ProAMC | 0.11 ± 0.01 (4) | 3.1 ± 0.4 (9) | 0.04 ± 0.00 |
| Glp-Phe-ProNH$_2$ | 1.64 ± 0.14 (5) | 55 ± 8 (3) | 0.03 ± 0.00 |
| Glp-His-ProOH | 4.43 ± 0.24 (3) | *311 ± 31 (5) | 0.01 ± 0.00 |

*From Ref. 23

Comparison of kinetic parameters for selected library peptides hydrolyzed by TRH-DE. The Michaelis constant for Glp-His-ProAMC (TRHAMC) was measured directly, whereas the K$_m$ values for the library peptides were measured indirectly by treating them as competitive inhibitors of TRHAMC hydrolysis by TRH-DE. The K$_m$ values were all determined by non-linear regression analysis of data obtained from the discontinuous fluorometric TRH-DE assay, as detailed in the text, and represent the mean±S.D. The number of determinations is shown in brackets. Included for comparison is the corresponding K$_m$ values for TRH and TRH-OH which the inventor recently published (23). V$_{max}$ values were estimated from rates of hydrolysis measured by HPLC using the relationship V$_{max}$=v$_o$ {(K$_m$+[S])/[S]}.

TABLE IV

| Peptide | % inhibition | K$_i$ (μM) |
| --- | --- | --- |
| Glp-Asn-ProNH$_2$ | 97 | 17.5 ± 1.4 |
| Glp-Gln-ProNH$_2$ | 83 | 69.0 ± 4.4 |
| Glp-Trp-ProNH$_2$ | 71 | 232 ± 26 |
| Glp-Phg-ProNH$_2$ | 57 | 356 ± 19 |
| Glp-homoPro-ProNH$_2$ | 40 | 500 ± 133 |
| Glp-Glu-ProNH$_2$ | 17 | >1000 |
| Glp-Gly-ProNH$_2$ | 8 | >1000 |
| Glp-Pro-ProNH$_2$ | 3 | >1000 |
| Glp-D-Asn-ProNH$_2$ | 2 | >1000 |
| Glp-Asp-ProNH$_2$ | 1 | >1000 |

Inhibitory effects of library peptides that were not hydrolyzed by TRH-DE. Data were obtained using TRHMCA as substrate in the continuous coupled assay. The % inhibition produced by each peptide (1 mM) was determined in the presence of 5 μM substrate. K$_i$ values (mean±S.D (n=3)) were measured by the continuous coupled assay at five different TRHAMC concentrations and at least three different concentrations of peptide. K$_i$ values for peptides displaying <20% inhibition were estimated to be >1 mM as described in the text. The K$_i$ for Glp-Asn-ProNH$_2$ represents the mean±S.D of three separate experiments using three different batches of Glp-Asn-ProNH$_2$—one batch was obtained from the American Peptide Company (U.S.A) and the other two batches were synthesized as described in Example 1 herein. No significant difference was found in the K$_i$ between the three different batches.

Initially, improvement in binding affinity of Glp-Asn-ProNH$_2$ was achieved by substituting the amino group at the C-terminus with 7-amino-4-methyl coumarin. Comparison of the binding affinities of these two compounds is shown below:

TABLE V

Inhibition of TRH-DE activity by Glp-Asn-ProNH$_2$ and Glp-Asn-ProAMC

| Peptide | % inhibition | K$_i$ (μM) |
| --- | --- | --- |
| Glp-Asn-ProAMC (1 μM) | 50 | 0.97 ± 0.08 |
| Glp-Asn-ProNH$_2$ (1 mM) | 97 | 17.5 ± 1.4 |

Data were obtained using TRHAMC as substrate in a continuous coupled assay (23). The % inhibition produced by 1 μM Glp-Asn-ProAMC and 1 mM Glp-Asn-ProNH$_2$ was determined in the presence of 5 μM substrate. K$_i$ values (mean±S.D (n=3)) were measured by the continuous coupled assay at five different TRHAMC concentrations and at least three different concentrations of peptide. The K$_i$ for Glp-Asn-ProNH$_2$ represents the mean±S.D of three separate experiments using three different batches of Glp-Asn-ProNH$_2$.

Figure 4:
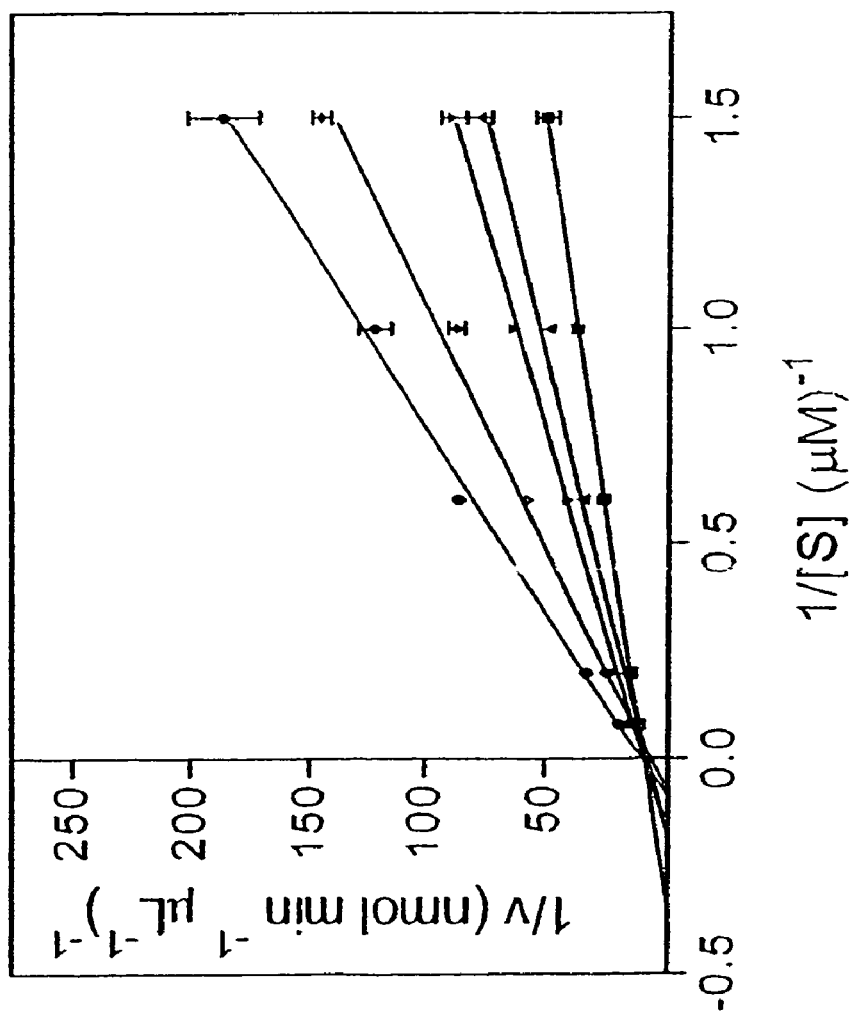
FIG. 4. Lineweaver-Burk plot for inhibition of TRH-DE hydrolysis of TRHAMC by Glp-Asn-ProAMC. Initial rates were determined using a continuous fluorometric assay. Data are shown as a Lineweaver-Burk plot for illustrative purposes and represent the mean±SEM (3). Error bars can be seen where the SEM is greater than the size of the symbol.

Lineweaver-Burk plots of the data obtained, shown in FIGS. 3 and 4, demonstrate that both Glp-Asn-ProAMC and Glp-Asn-ProNH$_2$ act as a simple competitive inhibitors of TRH-DE activity, in vitro.

Having regard to the literature references cited herein, including in particular the patent documents whose contents are incorporated herein by reference, the peptide derivatives of formula I and pharmaceutically acceptable salts thereof would be expected to inhibit TRH-DE activity, in vitro, in a manner similar to that described and may be synthesized by adapting the standard preparations presented, as appropriate.

The properties of Asn in the P$_1$' position of TRH were found to be unique as this was the only analogue that displayed a greater binding affinity for TRH-DE than TRH and was not hydrolysed by TRH-DE. It is not obvious why Glp-Asn-ProNH2 and Glp-Gln-ProNH2 are not TRH-DE substrates, but it might be postulated that binding of these peptides to the enzyme is distorted, thus preventing catalysis. Although this invention is not limited by any theory, and the test results were not predictable, it is possible to two-dimensionally superimpose the side chain of L-Asn onto that of L-His such that the amide NH$_2$ group of L-Asn overlaps with the τN of L-His. Similarly, the side chain of L-Gln can be two-dimensionally superimposed onto that of L-His such that the amide NH$_2$ group of L-Gln overlaps with the πN of L-His. However, the binding of Glp-Gln-ProNH$_2$ is not as favourable as that for Glp-Asn-ProNH$_2$ and Glp-His-ProNH$_2$. Since the TRH-like peptides which contain Asn, Gln and His in the P$_1$' position all bind relatively well to TRH-DE, it could be suggested that the nitrogen atoms in these side chains represent recognition moieties for the S$_1$' subsite of the enzyme and facilitate binding. The more favourable inhibitory properties of Glp-Asn-ProNH$_2$ compared to Glp-Gln-ProNH$_2$ may be related to the position of the nitrogen atom in the side chain and to the position of amide carbonyl group relative to the S$_1$' subsite on the enzyme. The enhanced binding of the coumarin derivative of Glp-Asn-ProNH$_2$ could be due to more favourable hydrophobic interactions occurring between the C-terminus of the peptide and the enzyme. Indications that this substitution would improve inhibitor binding were deduced from comparison of the kinetic parameters, which were determined in the inventor's laboratory, for TRH, TRHAMC and TRH-OH (Table III). From these kinetic parameters it was concluded that the addition of a large hydrophobic group, such as AMC, to the C-terminus of TRH would be a useful feature to incorporate into an TRH-DE inhibitor.

The resulting compound, Glp-Asn-ProAMC, was found to have a K$_i$ of 0.97±0.08 μM and is a potent, competitive TRH-DE inhibitor. Previously, the most potent TRH-DE inhibitor to be reported was CPHNA (26). This compound, though substantially structurally different from TRH and Glp-Asn-ProAMC, was found to inhibit TRH-DE in a competitive manner with a K$_i$ of 8 μM (21).

The influence of the C-terminal residue of Glp-Asn-Pro on binding to TRH-DE was examined further by synthesising and testing several compounds having an N-substituted amide group at the C-terminus of Glp-Asn-Pro similar to AMC. These compounds were synthesised using solution phase peptide chemistry as described above.

TABLE VI

HPLC analysis of Glp-Asn-Pro amides.

| Identity of C-terminal amide | Retention times (min) on HPLC |
|---|---|
| Benzylamide | 14.31 |
| p-anisidide | 14.99 |
| 5,6,7,8-tetrahydro-1-naphthylamide | 19.31 |
| 5-chloro-2-methoxy anilide | 19.59 |
| m-anisidide | 15.87 |
| o-anisidide | 15.41 |
| 2-aminophenol | 13.20 |
| 5-amino-2-methoxyphenol | 12.84 |
| 1,2,3,4-tetrahydro-1-naphthylamide isomer 1 | 18.07 |
| 1,2,3,4-tetrahydro-1-naphthylamide isomer 2 | 18.36 |
| 2-aminobenzyl alcohol | 11.87 |

All of the peptides shown above were synthesised in the inventor's laboratory. All were analysed and judged to be homogeneous by HP LC. HPLC analysis was conducted employing a Thermo Separation Products Spectra System HPLC. Peptides were eluted from a C-18 reverse-phase HPLC column using a linear gradient of 0-70% acetonitrile in 0.08% trifluoroacetic acid over a period of 30 min. UV absorbance was measured at 206 nm. Retention times (min) are shown for each of the peptides. Each of the Glp-Asn-Pro amides were tested for their ability to act as TRH-DE substrates using the HPLC assay described previously. None of these peptides were hydrolysed by TRH-DE. The ability of the Glp-Asn-Pro amides to inhibit TRH-DE activity was determined using the continuous coupled assay described previously (Table VI). Most of the carboxamides of Glp-Asn-Pro that were tested were found to display K$_i$ values for TRH-DE in the low μM range (Table VI) below that of Glp-Asn-ProNH$_2$. Nevertheless, all of the carboxamides of Glp-Asn-Pro that were tested displayed greater affinity for TRH-DE than TRH.

TABLE VII

Inhibition of TRH-DE activity by Glp-Asn-Pro amides.

| Identity of C-terminal amide | K$_i$ (μM) |
|---|---|
| Benzylamide | 11.87 |
| p-anisidide | 3.24 |
| 5,6,7,8-tetrahydro-1-naphthylamide | 9.31 |
| 5-chloro-2-methoxy anilide | 9.95 |
| m-anisidide | 0.86 |
| o-anisidide | 11.59 |
| 2-aminophenol | 6.62 |
| 5-amino-2-methoxyphenol | 1.72 |
| 1,2,3,4-tetrahydro-1-naphthylamide isomer 1 | 63.24 |
| 1,2,3,4-tetrahydro-1-naphthylamide isomer 2 | 22.37 |
| 2-aminobenzyl alcohol | 20.65 |
| 7-amido-4-methyl coumarin | 0.41 |

Data were obtained using TRH-AMC as substrate in the continuous coupled assay (23). The percent inhibition (i) produced by each peptide was measured in duplicate in the presence of 5 μM substrate. K$_i$ values were calculated using the equation: i=[I]/[I]+K$_i$(1+[S]/K$_m$) where K$_m$ is the Michaelis constant for the substrate TRH-AMC (23). The K$_i$ value of Glp-Asn-Pro-AMC was determined also by non-linear regression analysis of inhibition data from the continuous assay performed at five different TRH-AMC concentrations and three different concentrations of Glp-Asn-Pro-AMC (see Table V). HPLC analysis revealed that none of the peptides shown in the table above were hydrolysed by TRH-DE.

The influence of extension of the C-terminal residue of Glp-Asn-Pro on binding to TRH-DE was examined by synthesising and testing compounds with a large hydrophobic group on the C-terminus. The results are as follows:

TABLE VIII

K$_i$ values for C-terminally extended analogues of Glp-Asn-Pro-NH$_2$

| Peptide | K$_i$ (μM) | Retention Times (mins) |
|---|---|---|
| Glp-Asn-Pro-NH$_2$ | 17.5[a] | As before |
| Glp-Asn-Pro-Tyr-NH$_2$ | 10.29[b] | 11.3 |
| Glp-Asn-Pro-Trp-Ser-Tyr-NH$_2$ | 8.11[b] | 17.5 |
| Glp-Asn-Pro-Trp-Tyr-NH$_2$ | 5.91[b] | 17.3 |
| Glp-Asn-Pro-Trp-NH$_2$ | 5.17[b] | 15.7 |
| Glp-Asn-Pro-AMC | 0.97[a] | As before |
| Glp-Asn-Pro-Tyr-Trp-NH$_2$ | 0.78[b] | 16.9 |
| Glp-Asn-Pro-Trp-AMC | 0.08[b] | 22.7* |
| Glp-Asn-Pro-Tyr-Trp-AMC | 0.04[a] | 23.2* |

K$_i$ values were determined either by non-linear regression analysis of data obtained from the continuous coupled assay in which five different substrate concentrations and at least three different inhibitor concentrations were used [a] or from the percent inhibition (n = 3) produced in the presence of 5 μM substrate [b]. The errors in reproducing the K$_i$ values were not >10%.

The K$_i$ for Glp-Asn-Pro-NH$_2$ represents the mean of three separate experiments using three different batches which were synthesised either by standard Fmoc peptide chemistry in the inventor's laboratory or by The American Peptide Company as described above. HPLC analysis revealed that none of the peptides shown in the table above were hydrolysed by TRH-DE. HPLC was carried out similarly to the method described above with the acetonitride gradient extended to 40 mins in the case of peptides labelled by *.

These results indicate that there is great potential to improve potency by optimising binding to what appears to be a large hydrophobic binding pocket in the area of TRH-DE to which the C-terminus of TRH-DE inhibitors bind.

Preliminary evaluation of the functional effects of two TRH-DE inhibitors of the present invention in vivo. A preliminary assessment of the ability of pyroglutamyl-asparaginyl-prolineamide (Glp-Asn-ProNH$_2$, K$_i$=17.5 μM) and Glp-Asn-Pro-7amido-4-methyl coumarin (Glp-Asn-ProAMC, K$_i$=0.97 μM) to enhance TRH central actions in vivo was carried out using two different modes of administration. Charli et al. found that CPHNA increased the recovery of TRH from rat brain slices in vitro (26), indicating that TRH levels can be altered by inhibition of TRH-DE activity. The biological effects of TRH-DE inhibitors in vivo, however, have never been reported.

TRH has been shown to penetrate mouse brain after intravenous, intraperitoneal (i.p.), intramuscular, oral or rectal administration (33). Systemic administration of TRH has been shown to produce several distinctive behavioural responses in rats. These include body shaking behaviour, often referred to as 'wet dog shakes' (WDS) (34, 35) and increased grooming activity (36). The mechanism by which TRH produces these effects is not fully understood. It has been suggested that the manifestation of such behaviours in the rat following intrathecal administration of TRH results from an action at the level of the spinal cord and brainstem and is facilitated by a tonically active noradrenergic pathway via $α_1$-adrenoreceptors, (37). Also, that WDS in response to i.c.v injection of TRH are dependent on brain DA (38) and that the raphe-spinal 5-HTergic projection system may serve to modulate WDS elicited by systemic administration of TRH (39). By protecting endogenous TRH or exogenously administered TRH from degradation, TRH-DE inhibitors would be expected to amplify these effects.

Materials: Glp-Asn-ProNH$_2$ and Glp-Asn-ProAMC, were custom synthesized by the American Peptide Company (U.S.A.). TRH (Glp-His-ProNH$_2$) was obtained from Sigma-Aldrich. $^3$[H]-3-MeHis-TRH was purchased from New England Nuclear.

Methods: Behavioural studies were conducted using experimentally naïve Male Wistar rats (200-250 g) maintained in a temperature controlled (21° C.), artificially-lighted (12 hr light cycle) room with free access to food and water.

Behavioural effects of TRH±Glp-Asn-ProAMC following intra-cerebroventricular (i.c.v.) administration: Animals were implanted with guide cannula aimed at the lateral cerebral ventricles (AP—0.92 mm, ML—1.5 mm, DV—2.6 mm relative to Bregma, atlas of Paxinos & Watson) under halothane anaesthesia. One week following surgery placement of the cannulae was assessed by the ability of a microinjection of angiotensin II (200 ng in 1 μl) to induce drinking behaviour. Seven days later animals that exhibited a drinking response were placed in a perspex cage for 20 minutes. They were then administered either vehicle (1 μl 0.9% saline) or Glp-Asn-ProAMC (5 μg in 1 μl) followed 1 minute later by vehicle (1 μl 0.9% saline) or TRH (5 μg in 1 μl). One minute after the last i.c.v. injection animals were placed back into the perspex cage and their behaviour monitored by a computer automated tracking system for 30 minutes (Ethovision Pro, Noldus) to provide measures of locomotor activity. Animals were videotaped for subsequent blind analysis of WDS behaviour by a trained observer. A threshold dose of 5 μg TRH was chosen for i.c.v. administration so that if Glp-Asn-ProAMC enhanced responses to TRH, this would be clearly visible.

Behavioural effects of TRH±TRH-DE inhibitor following intraperitoneal (i.p.) administration: On the day of the experiment, animals were singly housed in perspex cages (30×20×20 cm) and allowed to acclimatize for 20 min. After this period, two baseline measurements of behaviour were made at 10 and 5 min prior to administration of drugs. At time 0, animals were injected i.p. with either vehicle (0.9% saline), 10 mg/kg TRH, 10 mg/kg Glp-Asn-ProNH$_2$, 10 mg/kg Glp-Asn-ProAMC or 10 mg/kg TRH+10 mg/kg Glp-Asn-ProAMC. Animals were then observed by two independent observers who were blind to treatment, every 5 min for 30 sec. Blocks of 5 animals were treated at a time, 1 per drug group. Blocks were repeated 5 times.

The occurrence of individual behaviours were noted using a behavioural check list, which included grooming, locomotion, rearing, chewing, sniffing, head weave, tail elevation, and/or straub tail and WDS behaviours. These behaviours were summed to yield an overall activity count. Animals were videotaped for separate subsequent analysis of WDS. All WDS behaviours occurring during each 5 min interval after drug administration were counted.

Since Glp-Asn-ProAMC was the more potent of the two TRH-DE inhibitors it was selected for evaluation alone and in combination with TRH for both modes of administration in this preliminary study.

Evaluation of the ability of TRH, Glp-Asn-ProNH$_2$, and Glp-Asn-ProAMC to bind to $^3$H-3MeHis-TRH-labelled receptors in rat cortex: Radioligand binding assays were conducted to investigate the possibility that the two TRH-DE inhibitors might exert their effects by acting independently at TRH receptors in the brain.

Cortex tissue from male Sprague-Dawley rats (250 g) was dissected out, weighed and homogenised in 30 volumes of ice-cold sodium phosphate buffer (0.02 M, pH 7.5). The homogenates were centrifuged at 30,000 g at 4° C. for 30 min. The supernatant was discarded and the pellet was resuspended at 100 mg wet wt/ml in buffer containing 177 μM bacitracin. The affinities of TRH and each of the TRH-DE inhibitors for rat cortical membranes were determined in competition binding experiments essentially as described previously by Vonhof et al., (40) using 6-8 nM $^3$H-3MeHis-TRH. Non-specific binding was defined in the presence of 10 μM TRH.

Analysis of Data

The statistical significance of differences between behavioural effects of treatments was determined using the Student's t-test or ANOVA, followed by a post-ANOVA test, as indicated. Radioligand binding data were analysed using non-linear curve fitting software (Prism, Graph Pad Software Inc.). IC$_{50}$ values calculated from competition experiments were converted to K$_i$ values using the Cheng-Prusoff (41) equation K$_i$=IC$_{50}$/(1+L/K$_d$), where L=ligand concentration and K$_d$=the apparent dissociation constant for [$^3$H]-[3-MeHis]TRH.

Results and Discussion

Figure 5:
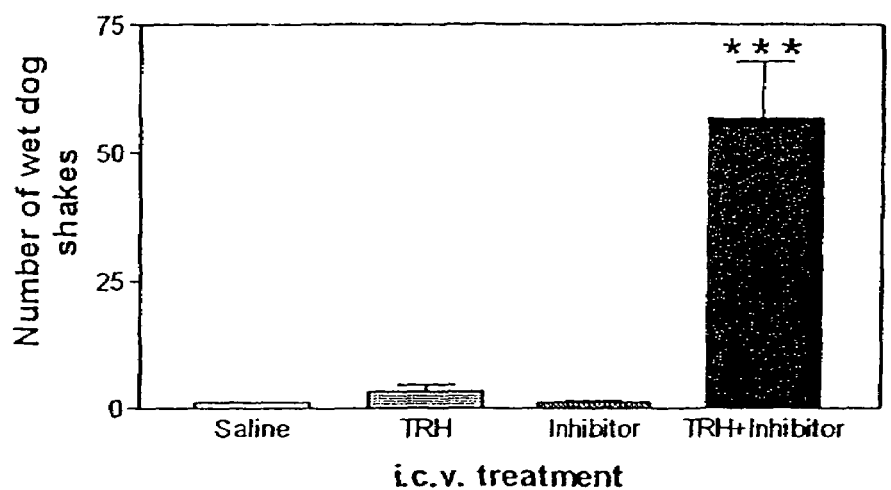
FIG. 5. Diagram of test results showing effect of i.c.v. administration of TRH±Glp-Asn-ProAMC on Wet Dog Shake (WDS) behaviour in rats. Male Wistar rats received an injection of either vehicle (1 µl 0.9% saline)+vehicle; Glp-Asn-ProAMC (5 µg in 1 µl)+vehicle; TRH (5 µg in 1 µl)+vehicle; or TRH (5 µg in 1 µl)+Glp-Asn-ProAMC (5 µg in 1 µl). Animals were then placed in individual cages and observed for 30 min. Data are expressed as mean±S.E. of WDS/30 min (n=6). ***p<0.001 vs TRH, one-way ANOVA followed by a post-ANOVA Bonferroni test.
Figure 6:
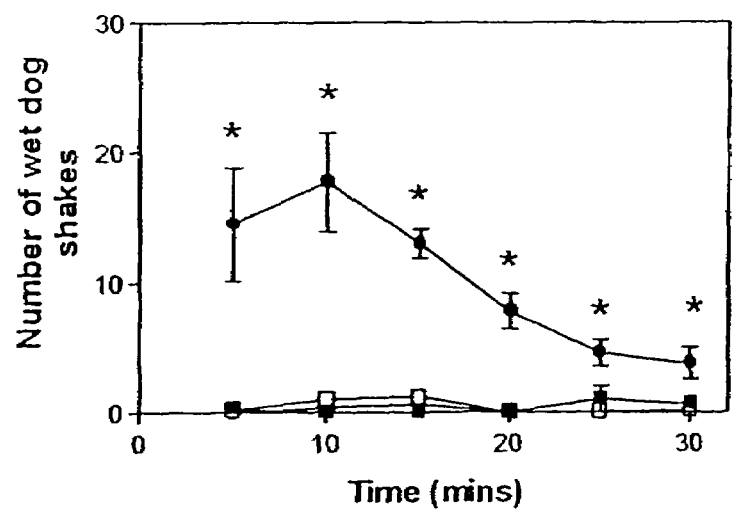
FIG. 6. Diagram of test results showing time course of effect of i.c.v. administration of TRH (5 µg in 1 µl)±Glp-Asn-ProAMC (5 µg in 1 µl) on WDS in rats. Male Wistar rats received an injection of either vehicle+vehicle (■); Glp-Asn-ProAMC+vehicle (○); TRH+vehicle (□); or TRH+Glp-Asn-ProAMC (●) and were placed in individual cages and observed for 30 min. Data are expressed as mean±S.E. of WDS every 5 min for 30 min (n=6). *p<0.01 vs TRH, one-way ANOVA followed by a post-ANOVA Bonferroni test.

From FIG. 5 it can be seen that co-administration of Glp-Asn-ProAMC with TRH resulted in a significant (3.33±1.23 vs 56.83±11.06, n=6, p<0.001 one-way ANOVA followed by Bonferrroni test), 18-fold increase in the number of WDS observed during the observation period. Neither TRH nor Glp-Asn-ProAMC alone produced a significantly greater number of WDS than vehicle during the 30 min observation period (FIG. 5). Time dependent analysis revealed that the maximum increase in WDS occurred 10 min post administration ($p<0.01$, one-way ANOVA followed by a post-ANOVA Bonferrroni test) and steadily declined with time, but still remained significant after 30 min (FIG. 6). At all time points the number of WDS observed in response to TRH+Glp-Asn-ProAMC was significantly greater than those observed in response to TRH alone ($p<0.01$, one-way ANOVA followed by post-ANOVA Bonferroni test) (FIG. 6). These data show that the central effects of exogenously administered TRH can be significantly enhanced by the presence of Glp-Asn-ProAMC and are consistent with exogenously administered TRH being protected from degradation by this TRH-DE inhibitor.

A significant increase in locomotion was not detected in response to either i.c.v. or i.p administration of TRH±TRH-DE inhibitors or Glp-Asn-ProNH$_2$ alone i.p. These results are consistent with Ervin et al., (36) who noted that groups reporting locomotor hyperactivity in response to either peripheral or intracerebral administration of TRH assess activity with photocells or electronic devices, which measure other behaviours in addition to locomotion.

Figure 7:
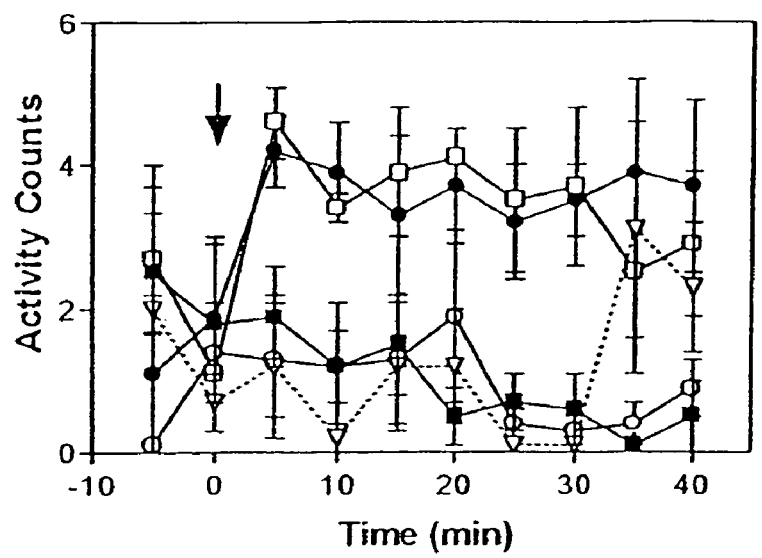
FIG. 7. Diagram of test results showing effects of TRH (10 mg/kg) and TRH-DE inhibitors (10 mg/kg), alone and in combination, on rat activity scores. Male Wistar rats were placed in individual cages and observed 10 and 5 min prior to i.p. injection with saline (■), Glp-Asn-ProNH$_2$ (▽), Glp-Asn-ProAMC (○), TRH (□) or TRH+Glp-Asn-ProAMC (●). They were then observed for 30 sec every 5 min for an additional 40 min. The occurrence of individual behaviours were noted using a behavioural check list and these behaviours were summed to yield an overall activity count. Points are the mean±S.E. of 5 experiments. Arrow indicates time of injection.

FIG. 7 shows that following i.p. administration, TRH caused a significant ($p<0.01$, Repeated Measures ANOVA followed by post-ANOVA Dunnett test) increase in rat activity scores throughout the 40 min period post injection. Analysis of the individual behaviours contributing to the activity score revealed that, in addition to WDS, TRH primarily promoted grooming, sniffing, and chewing behaviours. The activity scores of the animals treated with TRH together with Glp-Asn-ProAMC were also significantly higher than saline-treated rats ($p<0.01$, Repeated Measures ANOVA followed by post-ANOVA Dunnett test). It can also be seen from FIG. 7 that behavioural responses to TRH alone tended to decline 35 min after i.p. administration, whereas animals treated with TRH plus Glp-Asn-ProAMC showed no such decrease. Again, these results would be consistent with Glp-Asn-ProAMC protecting exogenously administered TRH from degradation. Animals treated with Glp-Asn-ProNH$_2$ i.p. showed significantly increased activity counts ($p<0.05$, Repeated Measures ANOVA followed by post-ANOVA Dunnett test) for the last 10 min of the observation period consistent with this inhibitor enhancing the actions of endogenous TRH in the central nervous system.

Figure 8:
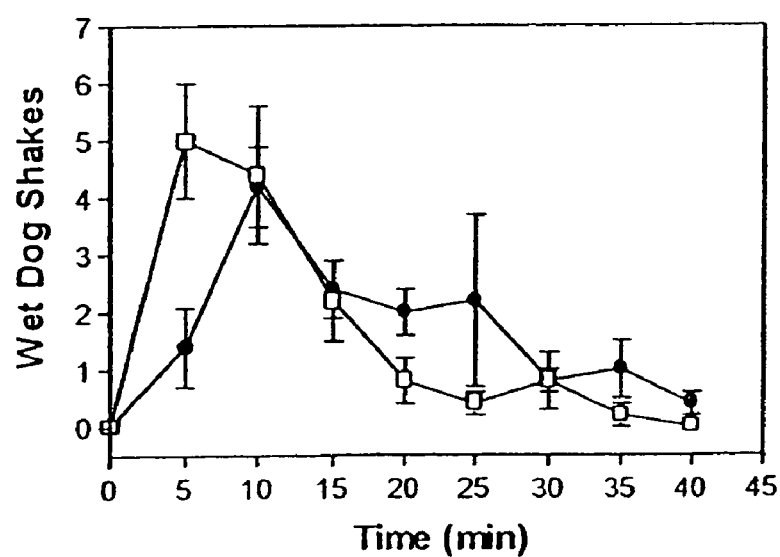
FIG. 8. Diagram of test results showing time course of effect of TRH±Glp-Asn-ProAMC on WDS behaviour in rats. Male Wistar rats were observed for 40 min following i.p. injection with TRH 10 mg/kg (□) or TRH 10 mg/kg±Glp-Asn-ProAMC 10 mg/kg (●). Points are the mean±S.E. of wet dog shakes/5 min (n=5). Saline treated animals exhibited no wet dog shakes at any time point.

Administration of TRH i.p. caused an immediate induction of WDS in all animals with the response gradually declining to zero after 40 min (FIG. 8). Induction of WDS in animals treated with TRH in combination with Glp-Asn-ProAMC was delayed by 5 min in comparison with TRH alone ($p<0.05$, Student's t-test) (FIG. 8). Nevertheless, administration of Glp-Asn-ProAMC with TRH resulted in a statistically significant enhancement of responses compared to TRH alone over the last 25 min of the observation period ($p<0.05$, 2-way ANOVA, FIG. 8).

Overall, the data show that the number of WDS observed in response to either i.c.v or i.p administration of TRH can be significantly enhanced by the presence of Glp-Asn-ProAMC and are consistent with exogenously administered TRH being protected from degradation by this TRH-DE inhibitor.

To investigate the possibility that the two TRH-DE inhibitors might exert their effects by acting independently at TRH receptors in the brain, radioligand binding assays were conducted to evaluate their ability to bind to high affinity receptors in rat brain cortex. In saturation binding experiments, [$^3$H]-3MeHis-TRH labelled a single population of sites in rat cortical membranes with an apparent dissociation constant ($K_d$) of $4.54\pm0.62$ nM (n=5). TRH competed for binding to [$^3$H]-3-MeHis-TRH-labelled TRH receptors in rat cortical membranes with a $pK_i$ of $7.65\pm0.17$ (n=7). In comparison, the $pK_i$ values for Glp-Asn-ProNH$_2$ and Glp-Asn-ProAMC were $5.15\pm0.24$ (n=6) and $4.32\pm0.24$ (n=3), respectively. Thus, both TRH-DE inhibitors were found to have low affinity compared to TRH for [$^3$H]-3MeHis-TRH-labelled receptors in rat cortical membranes, supporting the interpretation that inhibition of TRH-DE underpins the observed behavioural effects.

In conclusion, these studies demonstrate that. i.c.v. or i.p. administration of these novel, potent TRH-DE inhibitors potentiate the biological actions of TRH in the central nervous system in vivo. The results provide the first demonstration that TRH-DE inhibitors can potentiate the central biological actions of TRH in vivo.

Significance of these Studies

The results from these preliminary studies: (i) demonstrate that these novel TRH-DE inhibitors are parentally active in vivo at doses of 10 mg/kg i.p., and (ii) show that TRH-DE inhibitors are active in vivo when administered centrally (i.c.v.) at a dose of 5 μg indicating central sites of action.

It is considered, with support from the in vivo test results, that the TRH-DE inhibitors of the present invention will be valuable tools for investigating the biological roles of TRH-DE, and TRH, in the CNS and that they possess pharmacologically advantageous properties which will allow them to be used to potentiate the endogenous levels of TRH and/or to protect exogenously administered TRH or TRH analogues from degradation. This effect should have the potential to enhance therapeutic effectiveness of TRH or TRH analogues, particularly in the treatment of brain and spinal injury and certain CNS disorders.

Desirably, the invention will provide for use of a compound of Formula I$^a$ or a pharmaceutically acceptable salt thereof in the preparation of a medicament, particularly for the treatment of brain or spinal injuries or other central nervous system disorders or other TRH dependent disorders in tissues in which TRH-DE is the principal enzyme influencing TRH levels.

Desirably also, the invention will provide a method of treatment of brain or spinal injuries or other central nervous system disorders or other TRH-dependent disorders in tissues in which TRH-DE is the principal enzyme influencing TRH levels, which comprises administering to a patient suffering from such injuries or disorders an amount of a compound of Formula I$^a$ or a pharmaceutically acceptable salt thereof effective to potentiate endogenous TRH and/or protect exogenously administered TRH or TRH analogues from degradation by TRH-DE.

According to one aspect, the present invention provides pharmaceutical compositions comprising an effective amount, particularly a TRH-DE inhibiting effective amount, of a compound of Formula I or a pharmaceutically acceptable salt thereof. Normally the composition will also comprise a pharmaceutically acceptable carrier, particularly an inert carrier.

The compounds of the present invention may be administered by oral, parenteral, intramuscular (i.m.), intraperitoneal (i.p.), intravenous (i.v.) or subcutaneous (s.c.) injection, nasal, vaginal, rectal or sublingual routes of administration and can be formulated in dosage forms appropriate for each route of administration. Suitable dosage forms are known to those skilled in the art and are described, for example in U.S. Pat. No. 4,906,614 Giertz et. al or U.S. Pat. No. 5,244,884 Spatola et. al. Dosage levels should be sufficient to achieve the TRH-DE inhibiting effect required for treatment of the particular physical condition being treated.

REFERENCES

1. Bauer, K. (1994) *Eur. J. Biochem.* 224, 387-396.
2. O'Connor, B., and O Cuinn, G. (1985) *Eur. J. Biochem.* 150, 47-52.
3. Griffiths, E. C., Kelly, J. A., Ashcroft, A., and Robson, B. (1989) *Ann. N.Y. Acad. Sci.* 553, 217-231.
4. Wilk, S., and Wilk, E. K., (1989) *Neurochem. Int.* 15, 81-89.
5. Griffiths, E. C., (1985) *Psychoneuroendocrinol.* 10, 225-235.
6. Horita, A., Carino, M. A., and Lai, H. (1986) *Rev. Pharmacol. Toxicol.* 26, 311-332.
7. Horita, A. (1998) *Life Sci.* 62, 1443-1448.
8. Kelly, J. A. (1995) *Essays in Biochem.* 30, 133-149.
9. Bauer, K. (1995) *Metabolism of Brain Peptides* (O'Cuinn G., Ed.), pp. 201-213, CRC Press.
10. Charli, J. L., Cruz, C., Vargas, M. A., and Joseph-Bravo, P. (1988) *Neurochem. Int.* 13, 237-242.
11. Bauer, K., Heuer, H., Ifflander, F., Schmitmeier, S., Shomburg, L., Turwitt, S., and Wilkins, M. (1997) *Cell-Surface Peptidases in Health and Disease* (Kenny, A. J., and Boustead, C. M., Eds.), pp 239-248, BIOS Scientific Publishers Limited, Oxford, UK.
12. Charli, J. L., Vargas, M. A., Cisneros, M., De Gortari, P., Baeza, M. A., Jasso, P., Bourdais, J., Peréz, L., Uribe, R. M., and Joseph-Bravo, P. (1998) *Neurobiology* 6, 45-57.
13. Bauer, K., Carmeliet, P., Schulz, M., Baes, M., and Denef, C. (1990) *Endocrinology* 127, 1224-1233.
14. Cruz, C., Charli, J. L., Vargas, M. A., and Joseph-Bravo, P. (1991) *J. Neurochem.* 56, 1594-1601.
15. Heuer, H., Schäfer, M, K-H., and Bauer, K. (1998) *Thyroid.* 8, 915-920.
16. Turner, A. J. (1997) *Cell-Surface Peptidases in Health and Disease* (Kenny, A. J., and Boustead, C. M., Eds.), pp 239-248, BIOS Scientific Publishers Limited, Oxford, UK.
17. Lanzara, R., Liebman, M., and Wilk, S. (1989) *Ann. N.Y. Acad. Sci.* 553, 559-562.
18. O'Connor, B., and O'Cuinn, G. (1987) *J. Neurochem.* 48, 676-680.
19. Elmore, M. A., Griffiths, E. C., O'Connor, B., and O'Cuinn, G. O. (1990) *Neuropeptides* 15, 31-36.
20. O'Leary, R. M., and O'Connor, B. (1995) *Int. J. Biochem. Cell. Biol.* 27, 881-890.
21. Kelly, J. A., Loscher, C. E., Gallagher, S., and O'Connor, B. (1997) *Biochem. Soc. Trans.* 25, 114S.
22. Gallagher, S. P., and O'Connor, B. (1998) *Int. J. Biochem. Cell Biol.* 30, 115-133.
23. Kelly, J. A., Slator, G. R., Tipton, K. F., Williams, C. H., and Bauer, K. *Anal. Biochem.* 274, 195-202 (1999)
24. O'Cuinn, G., O'Connor, B., and Elmore, M. (1990) *J. Neurochem.* 54, 1-13.
25. Wilk, S. (1989) *Ann. N.Y Acad. Sci.* 553, 252-264.
26. Charli, J. L., Mendez, M., Vargas, M-A., Cisneros, M., Assai, M., Joseph-Bravo, P., and Wilk, S. (1989) *Neuropeptides.* 14, 191-196.
27. Schechter, I., and Berger, A. (1967) *Biochem. Biophys. Res Commun.* 27, 157-162.
28. Kelly J. A., Slator G. R., and Bauer K. (1999) J. Neurochem. Suppl. 73, S45.
29. Walker B (1994) *Peptide antigens-a practical approach* (Wisdom, G. B., Ed) pp 27-81, IRL Press, Oxford, U.K.
30. Zimmerman M. Ashe B., Yurewicz E. C. and Patel G., *Anal. Biochem.* (1977) 78, 47-51.
31. Fujiwara K. and Tsuru D., *J. Biochem.* (1978) 83, 1145-1149.
32. Dixon, M. and Webb, E. C. (1979) *Enzymes*, 3rd Ed., pp 72-75, Longman, London and Academic Press, New York, U.S.A.
33. Mitsuma, T and Nagimori, T(1983) Experientia 39, 620-622.
34. Yamada, K., Demarest, K. T., and Moore K. E., (1984) Neuropharmacol. 23, 735-739.
35. Bennett, G. W., Marsden, C. A., Fone, K. C. F., Johnson, J. V., and Heal, D. J. (1989) Ann. N. Y. Acad. Sci. 553, 106-120.
36. Ervin, G. N., Schmitz, S. A., Nemeroff, C. B. and Prange, A. J. Jr., (1981) Eur. J. Pharmacol. 72, 35-43.
37. Johnson, J. V., Fone, K. C. F., Havler, M. E., Tulloch, I. F., Bennett, G. W. and Marsden, C. A. (1989) Neuroscience 29, 463-470.
38. Drust E. G., and Connor, J. D. (1983) J. Pharmacol. Exp. Ther. 224, 148-154.
39. Funk, D., Post, R. M., and Pert, A. (1997) Psychopharmacology 133, 356-362.
40. Vonhof, S., Feuerstein, G., Cohen, L. A., and Labroo, V. M., (1990) Eur. J. Pharmnacol. 180, 1-12.
41. Cheng, Y. C. and Prusoff, W. H., (1973) Biochem. Pharmacol. 22, 3099-3108.

The invention claimed is:
1. A compound of formula I:

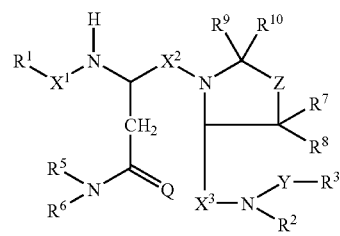

wherein:
$R^1$ is an optionally substituted 4-, 5- or 6-membered heterocyclic ring having one or more heteroatoms, in which at least one carbon atom of the ring is substituted with O, N, or S;
$X^1$ is —CO— or —CS— or —CH$_2$CO— or CH($R^4$) wherein $R^4$ is H or optionally substituted alkyl or —COOH or —COOR$^{11}$ wherein $R^{11}$ is optionally substituted alkyl;
$X^2$ and $X^3$ are independently —CO— or —CS—;
Z is —CH$_2$— or —S— or —O— or —NH—;
Q is O or S;
$R^2$ is H or optionally substituted alkyl or an optionally substituted carbocyclic ring;

$R^3$ is H or optionally substituted alkyl or an optionally substituted mono- or polycyclic ring, optionally having one or more heteroatoms in the ring(s) and optionally being a fused ring; or $R^2$ and $R^3$ together form an optionally substituted mono- or polycyclic ring optionally having one or more heteroatoms in the ring(s) and optionally being a fused ring;

$R^5$ and $R^6$ are independently H, or lower alkyl;

$R^7$ and $R^8$ are independently H, or optionally substituted lower alkyl;

$R^9$ and $R^{10}$ are independently H, or optionally substituted alkyl, or an optionally substituted carbocyclic ring;

Y is —$(CH_2)_n$— where n is 0, 1, 2 or 3 provided that when $R^2$ and $R^3$ form part of the ring n is 0;

provided that when $R^1$ is:

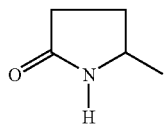

and $X^1$, $X^2$ and $X^3$ are —CO—
and $R^5$, $R^6$, $R^7$, $R^8$, $R^9$, $R^{10}$ are H
and Z is —$CH_2$—
and Q is O
and Y is —$(CH_2)_n$— where n is 0,
then $R^2$ and $R^3$ are not both H;

and pharmaceutically acceptable salts thereof.

2. The compound of claim 1, wherein $R^1$, $X^1$, $X^2$, $X^3$, Z, Q, $R^5$, $R^6$, $R^7$, $R^8$, $R^9$, $R^{10}$ and Y are as defined in claim 1, $R^2$ is H or optionally substituted alkyl or an optionally substituted carbocyclic ring, $R^3$ is optionally substituted alkyl or an optionally substituted mono- or polycyclic ring, optionally having one or more heteroatoms in the ring(s) and optionally being a fused ring;

or $R^2$ and $R^3$ together form an optionally substituted mono- or polycyclic ring optionally having one or more heteroatoms in the ring(s) and optionally being a fused ring; and pharmaceutically acceptable salts thereof.

3. The compounds of claim 1, wherein $R^2$ or $R^3$, or $R^2$ and $R^3$ together, represent an optionally substituted mono- or polycyclic ring.

4. The compound of claim 1, wherein $R^5$ and $R^6$ are H and Q is O, so that the compounds are thyrotropin-releasing hormone (TRH) derivatives having L-asparagine residue (Asn) in the $P_1'$ position.

5. The compound of claim 2, comprising L-asparagine (Asn) in the $P_1'$ position of the peptide with the general formula:

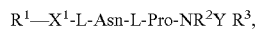

wherein $R^1$, $X^1$, $R^2$, Y and $R^3$ are as defined in claim 1.

6. The compound of claim 1, wherein Z is —$CH_2$— and $R^7$ and $R^8$ are H.

7. The compound of claim 1, wherein $X^1$, $X^2$ and $X^3$ are —C—.

8. The compound of claim 1, wherein $R^2$ or $R^3$, or $R^2$ and $R^3$ together, represent a large hydrophobic group, wherein a large hydrophobic group is a methyl coumarin.

9. The compound of claim 1, wherein the group —N($R^2$)$YR^3$ or the group $R^3$ is at least one optionally substituted amino acid residue.

10. The compound of claim 1, wherein $R^1$ is selected from any of the following:

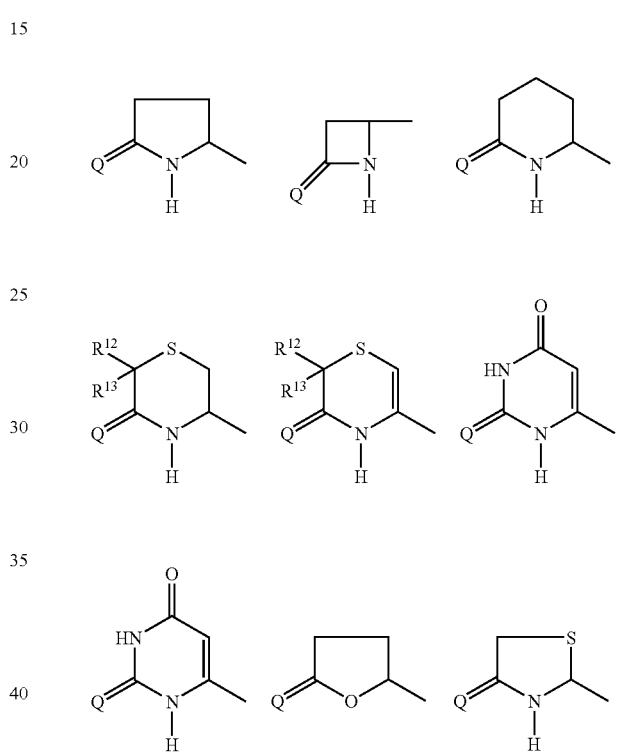

wherein $R^{12}$ is hydrogen, lower alkyl or phenyl, $R^{13}$ is hydrogen or lower alkyl, Q is O or S.

11. The compound of claim 10, wherein Q is O.

12. The compound of claim 1, wherein $R^1$ is a five-membered pyrrolidinone, thiazolidinone or butyrolactone ring.

13. The compound of claim 1, wherein $R^1$ is:

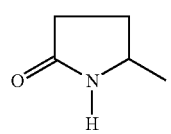

14. The compound of claim 1 having the formula:

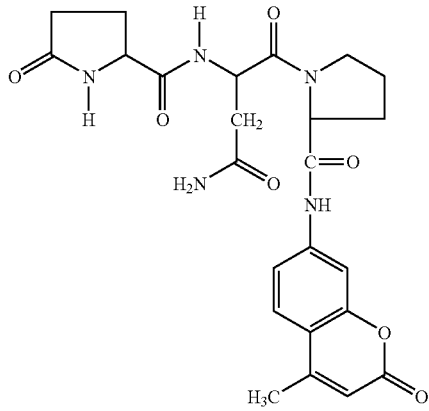

15. The compound of claim 1 having the formula (Glp-L-Asn-L-Pro-L-Tyr-L-TrpAMC):

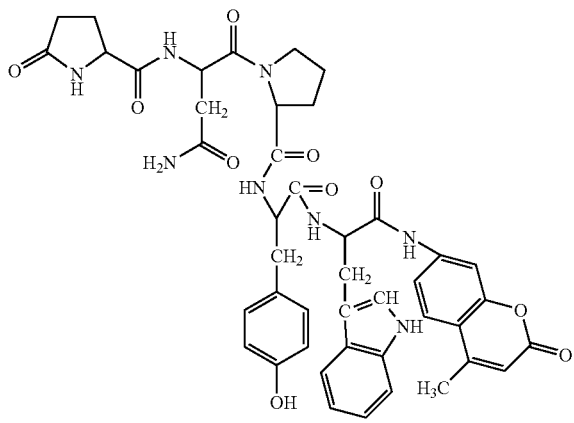

16. The compound of claim 1 having the formula:

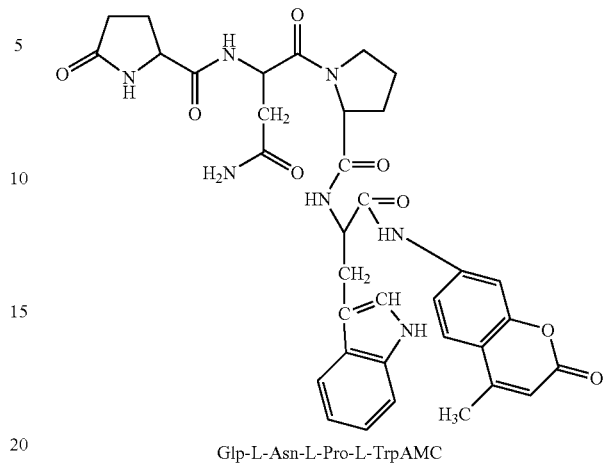

Glp-L-Asn-L-Pro-L-TrpAMC

17. The compound of claim 1 having the formula selected from the group consisting of Glp-Asn-Pro-isopropylamide, Glp-Asn-Pro-cyclohexamide, Glp-Asn-Pro-piperazide, Glp-Asn-Pro-5-amidoquinoline (or 6-amidoquinoline or 8-amidoquinoline), Glp-Asn-Pro-5-amido-isoquinoline, Glp-Asn-Pro-Anilide, Glp-Asn-Pro-7-amido(trifluoromethyl) coumarin, Glp-Asn-Pro-6-amido-3,4-benzocoumarin, Glp-Asn-Pro-1,2,3,4-tetrahydro-1-naphthylamide, Glp-Asn-Pro-5,6,7,8-tetrahydro-1-naphthylamide, Glp-Asn-Pro-benzylamide, Glp-Asn-Pro-2-thiazolamide, Glp-Asn-Pro-1-naphthylmethylamide, Glp-Asn-Pro-p-Anisidide, Glp-Asn-Pro-para amidobenzoic acid, Glp-Asn-Pro-m-anisidide, Glp-Asn-Pro-o-anisidide, Glp-Asn-Pro-5-chloro-2-methoxy anilide, Glp-Asn-Pro-3-hydroxy-4-methoxy anilide, Glp-Asn-Pro-2-hydroxy anilide, Glp-Asn-Pro-2-(hydroxymethyl-)anilide, Glp-Asn-Pro-4-trifluoromethyl anilide, Glp-Asn-Pro-Tyr-$NH_2$, Glp-Asn-Pro-Trp-Ser-Tyr-$NH_2$, Glp-Asn-Pro-Tyr-$NH_2$, Glp-Asn-Pro-Trp-$NH_2$, Glp-Asn-Pro-Tyr-Trp-$NH_2$, Glp-Asn-Pro-Trp-AMC, Glp-Asn-Pro-Tyr-Trp-AMC, Glp-Asn-Pro-Trp-Trp-AMC, Glp-Asn-Pro-Tyr-Trp-Trp-AMC, Glp-Asn-Pro-Phe-TyrAMC, Glp-Asn-Pro-Ala-TrpAMC, Glp-Asn-Pro-Val-Tyr-TrpAMC and pharmaceutically acceptable salts thereof.

18. The compound of claim 17, selected from the group consisting of Glp-Asn-Pro-1,2,3,4-tetrahydro-1-naphthylamide, Glp-Asn-Pro-5,6,7,8-tetrahydro-1-naphthylamide, Glp-Asn-Pro-benzylamide, Glp-Asn-Pro-p-anisidide, Glp-Asn-Pro-m-anisidide, Glp-Asn-Pro-o-anisidide, Glp-Asn-Pro-5-chloro-2-methoxy anilide, Glp-Asn-Pro-3-hydroxy-4-methoxy anilide, Glp-Asn-Pro-2-hydroxy anilide, Glp-Asn-Pro-2-(hydroxymethyl-)anilide, and pharmaceutically acceptable salts thereof.

\* \* \* \* \*

UNITED STATES PATENT AND TRADEMARK OFFICE
CERTIFICATE OF CORRECTION

PATENT NO.       : 7,378,397 B2
APPLICATION NO.  : 11/345649
DATED            : May 27, 2008
INVENTOR(S)      : Julie A. Kelly It is certified that error appears in the above-identified patent and that said Letters Patent is hereby corrected as shown below:

In claim 7, column 40, line 2, delete "—C—" and insert -- —CO— -- therefor.

Signed and Sealed this

Twenty-ninth Day of July, 2008

JON W. DUDAS
*Director of the United States Patent and Trademark Office*